United States Patent [19]

Raeymaekers et al.

[11] Patent Number: 5,039,677
[45] Date of Patent: Aug. 13, 1991

[54] 6-(1H-AZOL-1-YLMETHYL)-1-(PYRIMIDINYLOXY)-1H BENZOTRIAZOLES

[75] Inventors: Alfons H. M. Raeymaekers, Beerse; Eddy J. E. Freyne, Rumst; Josephus L. H. Van Gelder, Kasterlee, all of Belgium; Marc G. Venet, Paris, France

[73] Assignee: Janssen Pharmaceutica N.V., Montreal, Canada

[21] Appl. No.: 537,831

[22] Filed: Jun. 13, 1990

Related U.S. Application Data

[60] Division of Ser. No. 415,440, Oct. 28, 1989, Pat. No. 4,943,574, which is a continuation of Ser. No. 223,486, Jul. 25, 1988, abandoned, which is a continuation-in-part of Ser. No. 194,775, May 17, 1988, abandoned, which is a continuation-in-part of Ser. No. 56,021, Jun. 1, 1987, abandoned.

[51] Int. Cl.$^5$ ................. C07D 403/14; A61K 31/505
[52] U.S. Cl. .................... 514/269; 544/298; 544/316; 544/319; 548/238
[58] Field of Search ............... 514/269; 544/316, 319, 544/298

[56] References Cited

U.S. PATENT DOCUMENTS

| | | | |
|---|---|---|---|
| 4,602,025 | 7/1986 | Hirsch et al. | 514/359 |
| 4,609,666 | 9/1986 | Hirsch et al. | 514/359 |
| 4,634,704 | 1/1987 | Janssens et al. | 514/369 |
| 4,826,862 | 5/1989 | Raeymaekers et al. | 514/383 |
| 4,859,684 | 8/1989 | Raeymaekers et al. | 514/365 |

Primary Examiner—Donald G. Daus
Attorney, Agent, or Firm—Charles J. Metz

[57] ABSTRACT (1H-azol-1-ylmethyl)substituted benzotriazole derivatives, compositions containing the same, and methods of treating estrogen dependent disorders.

6 Claims, No Drawings

6-(1H-AZOL-1-YLMETHYL)-1-(PYRIMIDINYLOXY)-1H BENZOTRIAZOLES

CROSS-REFERENCE TO RELATED APPLICATIONS

This application is a divisional of application Ser. No. 415,440, filed Sept. 28, 1989, now U.S. Pat. No. 4,943,574 which was a continuation of application Ser. No. 223,486, filed on July 25, 1988, now abandoned, which was a continuation-in-part of application Ser. No. 194,775, filed on May 17, 1988, now abandoned, which was a continuation-in-part of application Ser. No. 56,021, filed on June 1, 1987, now abandoned.

BACKGROUND OF THE INVENTION

A large number of azole derivatives are known in the art as antifungal agents. Recently miconazole, clotrimazole and ketoconazole, members of a class of imidazole agents with a broad spectrum activity against a variety of yeasts, dermatophytes and dimorphous fungi, have been reported to inhibit the action of the enzyme aromatase in Biochemical Pharmacology, 34, 1087 (1985).

Related azole derivatives have been described in U.S. Pat. Nos. 4,602,025 and 4,609,666 and in the Published European patent application 0,165,781 as aromatase inhibitors useful for treating estrogen dependent diseases.

In U.S. Pat. No. 4,410,539 there are further described a number of (1H-imidazol-1-ylmethyl) substituted indole derivatives which compounds are useful as thromboxane synthetase inhibitors.

The compounds of the present invention differ therefrom by the fact that they contain invariably a benzotriazole moiety and by their capability to inhibit the action of the enzyme aromatase. The compounds of the present invention are therefore useful in therapeutically treating and preventing estrogen hormone dependent disorders in mammals.

DESCRIPTION OF THE INVENTION

The present invention is concerned with benzotriazole derivatives of formula

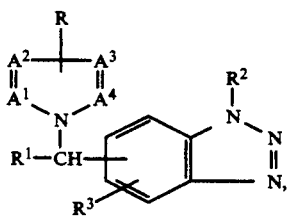

the pharmaceutically acceptable acid addition salts and stereoisomeric forms thereof, wherein $A^1=A^2-A^3=A^4$ is a bivalent radical having the formula —CH=N—CH=CH— (a-1), —CH=N—CH=N— (a-2), or —CH=N—N=CH— (a-3);

R is hydrogen or $C_{1-6}$alkyl;

$R^1$ is hydrogen, $C_{1-10}$alkyl, $C_{3-7}$cycloalkyl, $Ar^1$, $Ar^2—C_{1-6}$alkyl, $C_{2-6}$alkenyl or $C_{2-6}$alkynyl;

$R^2$ is hydrogen; $C_{1-10}$alkyl optionally substituted with $Ar^1$, $C_{3-7}$cycloalkyl, hydroxy or $C_{1-6}$alkyloxy; $Ar^1$; $C_{2-6}$alkenyl; $C_{2-6}$alkynyl; $C_{3-7}$cycloalkyl; bicyclo[2.2.1-]heptan-2-yl; 2,3-dihydro-1H-indenyl; 1,2,3,4-tetrahydronaphthalenyl; hydroxy; $C_{2-6}$alkenyloxy optionally substituted with $Ar^2$; $C_{2-6}$alkynyloxy; pyrimidinyloxy; di($Ar^2$)methoxy; (1-$C_{1-4}$alkyl-4-piperidinyl)oxy; or $C_{1-10}$alkyloxy optionally substituted with halo, hydroxy, $C_{1-6}$alkyloxy, amino, mono, and di($C_{1-6}$alkyl)amino, trifluoromethyl, carboxyl, $C_{1-6}$alkyloxycarbonyl, $Ar^1$, $Ar^2—O—$, $Ar^2—S—$, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl $R^3$ is hydrogen, nitro, amino, mono- and di($C_{1-6}$alkyl)amino, halo, $C_{1-6}$alkyl, hydroxy or $C_{1-6}$alkyloxy;

wherein $Ar^1$ is phenyl, substituted phenylm, naphthalenyl, pyridinyl, aminopyridinyl, imidazolyl, triazolyl, thienyl, halothienyl, furanyl, $C_{1-6}$alkylfuranyl, halofuranyl or thiazolyl; and $Ar^2$ is phenyl, substituted phenyl or pyridinyl, said substituted phenyl being phenyl substituted with up to 3 substituents each independently selected from halo, hydroxy, hydroxymethyl, trifluoromethyl, $C_{1-6}$alkyl, $C_{1-6}$alkyloxy, $C_{1-6}$alkyloxycarbonyl, carboxyl, formyl, (hydroxyimino)methyl, cyano, amino, mono- and di($C_{1-6}$alkyl)amino and nitro;

As used in the foregoing definitions the term halo is generic to fluoro, chloro, bromo and iodo; the term "$C_{1-6}$alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" is meant to include $C_{1-6}$alkyl radicals, as defined hereinabove, and the higher homologs thereof having from 7 to 10 carbon atoms; the term "$C_{3-7}$cycloalkyl" is generic to cyclopropyl, cyclobutyl, cyclopentyl, cyclohexyl and cycloheptyl. "$C_{2-6}$alkenyl" defines straight and branch chained hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{2-6}$alkynyl" defines straight and branch chained hydrocarbon radicals containing one triple bond and having from 2 to 6 carbon atoms such as, for example, 2-propynyl, 2-butynyl, 3-butynyl, 2-pentynyl, 3-pentynyl, 4-pentynyl and the like; and when a $C_{2-6}$alkenyl or a $C_{2-6}$alkynyl is substituted on a heteroatom, then the carbon atom of said $C_{2-6}$alkenyl or said $C_{3-6}$alkynyl connected to said heteroatom preferably is saturated.

It is to be understood that the

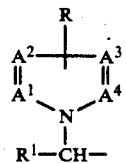

moiety, hereinafter refered as the 1H-azol-1-ylmethyl moiety, may be substituted on either the 4,5,6 or 7 position of the benzotriazole heterocyclic ring. In addition, the compounds of formula (I) may also contain in their structure a tautomeric system and consequently these compounds can be present in each of their tautomeric forms. Also within the scope of the invention are the compounds of formula (I) in the form of hydrates or in solvent addition forms.

An interesting group among the compounds of formula (I) comprises those compounds of formula (I) wherein $A^1=A^2-A^3=A^4$ is a bivalent radical having the formula (a-1).

Another interesting group among the compounds of formula (I) comprises those compounds of formula (I) wherein $A^1=A^2-A^3=A^4$ is a bivalent radical having a formula (a-2) or (a-3), with (a-2) being the most interesting subgroup.

Preferred compounds within the present invention are those compounds of formula (I) wherein R is hydrogen or $C_{1-4}$alkyl; $R^1$ is hydrogen; $C_{1-6}$alkyl optionally substituted with phenyl or substituted phenyl; $C_{3-7}$cycloalkyl; phenyl; substituted phenyl; pyridinyl; naphthalenyl; thienyl; furanyl; imidazolyl; triazolyl; $C_{2-6}$alkenyl or $C_{2-6}$alkynyl; $R^2$ is hydrogen; $C_{1-6}$alkyl optionally substituted with phenyl, substituted phenyl, naphthalenyl, thienyl, furanyl, $C_{1-4}$alkylfuranyl, $C_{3-7}$cycloalkyl, hydroxy or $C_{1-4}$alkyloxy; phenyl; substituted phenyl; $C_{2-6}$alkenyl; $C_{2-6}$alkynyl; $C_{3-7}$cycloalkyl; bicyclo[2.2.1]heptan-2-yl; 2,3-dihydro-1H-indenyl; 1,2,3,4-tetrahydronaphthalenyl; hydroxy; $C_{2-6}$alkenyloxy optionally substituted with phenyl; $C_{2-6}$alkynyloxy; pyrimidinyloxy; di(phenyl)methoxy; (1-$C_{1-4}$alkyl-4-piperidinyl)oxy; or $C_{1-6}$alkyloxy optionally substituted with halo, hydroxy, amino, mono-and di($C_{1-4}$alkyl)amino, trifluoromethyl, carboxyl, $C_{1-6}$alkyloxy-carbonyl, phenyl, substituted phenyl, thienyl, furanyl, pyridinyl, phenoxy, phenylthio, $C_{3-7}$cycloalkyl, 2,3-dihydro-1,4-benzodioxinyl, 1H-benzimidazolyl, $C_{1-4}$alkyl substituted 1H-benzimidazolyl, (1,1'-biphenyl)-4-yl, or with 2,3-dihydro-2-oxo-1H-benzimidazolyl; and $R^3$ is hydrogen or nitro.

Particularly preferred compounds within the present invention are those preferred compounds wherein the 1H-azol-1-ylmethyl moiety is substituted on either the 5 or 6 position of the benzotriazole heterocyclic ring.

More particularly preferred compounds within the present invention are those particularly preferred compounds wherein R is hydrogen; $R^1$ is hydrogen, $C_{1-6}$alkyl, phenyl or substituted phenyl; and $R^2$ is hydrogen; $C_{3-7}$cycloalkyl; bicyclo[2.2.1]heptan-2-yl; 2,3-dihydro-1H-indenyl; 1,2,3,4-tetrahydronaphthalenyl; $C_{1-6}$alkyl optionally substituted with phenyl, substituted phenyl or $C_{3-7}$cycloalkyl; or $C_{1-6}$alkyloxy optionally substituted with phenoxy, phenylthio, $C_{3-7}$cycloalkyl, phenyl or substituted phenyl.

Especially preferred compounds within the invention are those more particularly preferred compounds of formula (I) wherein $R^1$ is phenyl optionally substituted with halo, $C_{1-4}$alkyl, $C_{1-4}$alkyloxy or trifluoromethyl; and $R^2$ is $C_{1-6}$alkyl.

More especially preferred compounds within the invention are those especially preferred compounds of formula (I) wherein $R^1$ is phenyl or halophenyl and $R^2$ is $C_{1-4}$alkyl.

The most preferred compounds within the invention are selected form the group consisting of 6-[(1H-imidazol-1-yl)phenylmethyl]-1-methyl-1H-benzotriazole, 6-[(4-chlorophenyl)(1H-1,2,4-triazol-1-yl)methyl]-1-methyl-1-H-benzotriazole, the pharmaceutically acceptable acid addition salts and possible stereochemically isomeric forms thereof.

A particular subgroup of compounds of formula (I) comprises those compounds, preferred, particularly preferred and more particularly preferred compounds of formula (I) wherein $R^2$ is connected to the nitrogen atom of the benzotriazole ring on a carbon atom or wherein $R^2$ is hydrogen. Said compounds of formula (I) being represented hereinafter by compounds of formula (I-b).

Another particular subgroup of compounds of formula (I) comprises those compounds, preferred, particularly prefrred and more particularly preferred compounds of formula (I) wherein $R^2$ is connected to the nitrogen atom of the benzotriazole ring on an oxygen atom. Said compounds of formula (I) being represented hereinafter by compounds of formula (I-c).

The compounds of formula (I) can generally be prepared by N-alkylating an azole of formula (III) or an alkali metal salt thereof with a benzotriazole of formula (II).

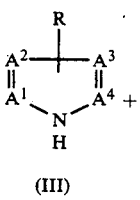

(III)

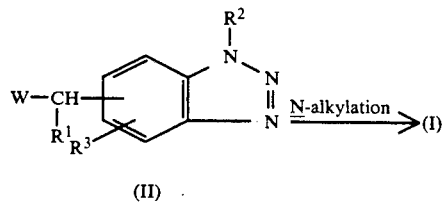

(II)

W as used in the reaction of (II) with (III) and in the following reaction schemes is an appropriate leaving group such as, for example, halo, preferably chloro, bromo or iodo, a sulfonyloxy group, e.g., methylsulfonyloxy or 4-methylbenzenesulfonyloxy.

The above described N-alkylation is conveniently carried out by stirring the reactants in the presence of a suitable organic solvent such as, for example, an aromatic hydrocarbon, e.g., benzene, methylbenzene, dimethylbenzene, and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethylacetamide (DMA), dimethyl sulfoxide (DMSO), 1-methyl-2-pyrrolidinone, acetonitrile, hexamethylphosphor triamide (HMPT), 1,3-dimethyl-3,4,-5,6-tetrahydro-2(1H)-pyrimidinone (DMPU), 1,3-dimethyl-2-imidazolidinone (DMEU), benzonitrile and the like; and mixtures of such solvents. Somewhat elevated temperatures may be appropriate to enhance the rate of the reaction and in some cases the reaction may even be carried out at the reflux temperature of the reaction mixture.

The addition of an appropriate base such as, for example, an alkali or an earth alkaline metal carbonate, hydrogen carbonate, hydroxide, amide or hydride, e.g., sodium hydroxide, potassium hydroxide, potassium carbonate, sodium hydride and the like or an organic base, such as, for example, N,N-dimethyl-4-pyridinamine, pyridine, N,N-diethylethanamine or N-(1-methylethyl)-2-propanamine may be employed to pick up the acid which is liberated during the course of the reaction. In some instances it may be advantageous to use an excess of the azole (III) or to convert it to its metal salt form, in particularly its alkali metal salt form following art-known procedures such as, e.g., by treatment of the azole (III) with an alkali metal hydroxide, alkoxide, or hydride.

Compounds of formula (I) wherein $A^1=A^2-A^3=A^4$ is a bivalent radical of formula (a-1), said compounds being represented by formula (I-a-1), may also be prepared by reacting a benzotriazole of formula (II) with a 1-protected imidazole of formula (III-a) following the N-alkylation procedures described hereinabove for the preparation of compounds of formula (I) starting from (II) and (III).

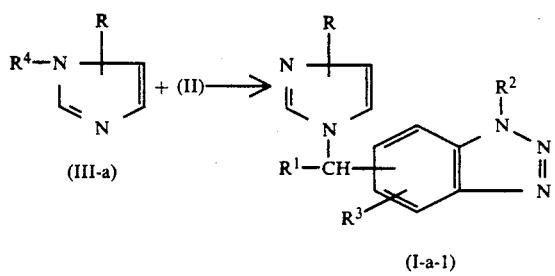

In (III-a) $R^4$ represents a protective group such as, for example, $C_{1-6}$alkylcarbonyl, $C_{1-6}$alkyloxycarbonyl, arylcarbonyl or a tri($C_{1-6}$alkyl)silyl group. In some instances the reaction of (III-a) with (II) first yields a 1-protected-imidazolium salt of formula (IV) which may in situ, or if desired, after isolating and further purifying it, be deprotected by stirring it in an aqueous basic solution.

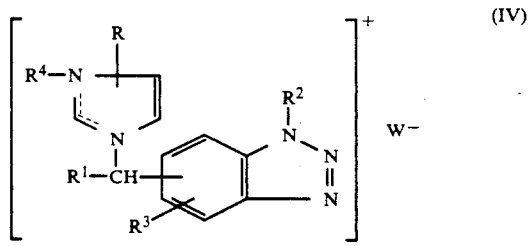

In (IV) $W^-$ is an anion arising from an acid such as, for example, hydrochloric acid, hydrobromic acid, methanesulfonic acid, 4-methylbenzenesulfonic acid and the like acids.

Particular compounds of formula (I) wherein $A^1=A^2-A^3=A^4$ is a bivalent radical of formula (a-2), said compounds being represented by formula (I-a-2), can also be prepared by N-alkylation of a triazolamine of formula (III-b) with a benzotriazole of formula (II) and subsequent deamination of the thus prepared triazolium salt of formula (V).

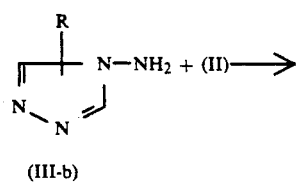

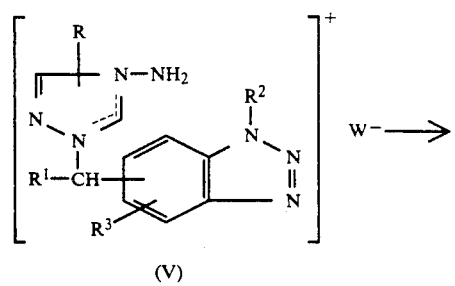

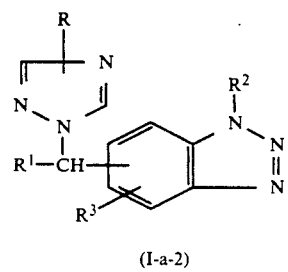

In (V) $W^-$ is an anion arising from an acid such as, for example, hydrochloric acid, hydrobromic acid, methanesulfonic acid, 4-methylbenzenesulfonic acid and the like acids.

The N-alkylation reaction of (III-b) with (II) is carried out according to similar procedures as described hereinabove for the preparation of a compound of formula (I) starting from (III) and (II). The said deamination reaction is conveniently conducted by means of an acidic nitrite solution in the presence of an appropriate reductant.

Preferably, the said deamination reaction is conducted with an aqueous solution of nitrous acid or of a nitrite salt in a suitable acid in the presence of a reducing agent such as, for example, hypophosphorous acid, formic acid, at a lower temperature.

The compounds of formula (I) may also be prepared by reacting an alcohol of formula (VI) with a reagent of formula (VII), such as, for example, a 1,1'-carbonylbis[1H-imidazole].

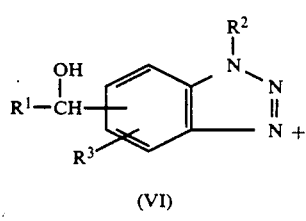

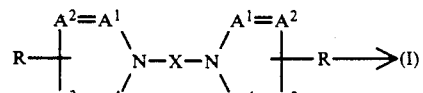

In (VII) X represents $$\mathord{>}C=O, \quad S \quad or \quad \mathord{>}C=O.$$

In some instances the reaction of (VI) with (VII) first yields an intermediate of formula (VIII) which may in situ or, if desired, after isolating and further purifying it, be converted to the desired compound of formula (I).

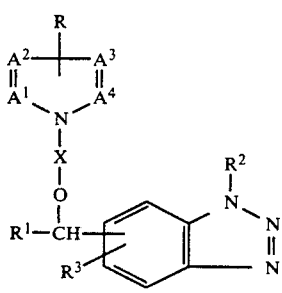

(VIII)

Said reaction may conveniently be conducted in a suitable solvent such as, for example, an ether, e.g., 1,4-dioxane, tetrahydrofuran; a halogenated hydrocarbon, e.g., di- or trichloromethane; a hydrocarbon, e.g., benzene, methylbenzene; a ketone, e.g., 2-propanone, 4-methyl-2-pentanone; N,N-dimethylformamide, N,N-dimethylacetamide, or mixtures of such solvents. In order to enhance the reaction rate, it may be advantageous to heat the reaction mixture.

The compounds of formula (I) can alternatively be prepared under similar conditions as are described in the literature for the preparation of benzotriazoles starting from appropriate benzenediamines or halonitrobenzene derivatives. Depending on the nature of the substituent $R^2$ in the compounds of formula (I) to be prepared, the following procedures may, for example, be utilized.

The compounds of formula (I) wherein $R^2$ is hydrogen; $C_{1-10}$alkyl optionally substituted with $Ar^1$, $C_{3-7}$cycloalkyl, hydroxy or $C_{1-6}$alkyloxy; $Ar^1$; $C_{2-6}$alkenyl; $C_{2-6}$alkynyl; $C_{3-7}$cycloalkyl; bicyclo[2.2.1]heptan-2-yl; 2,3-dihydro-1H-indenyl; or 1,2,3,4-tetrahydronaphthalenyl, said radical being represented by $R^{2-a}$ and said compounds by (I-b), may be derived from an appropriately substituted diamine of formula (IX) by diazotation and subsequent cyclization.

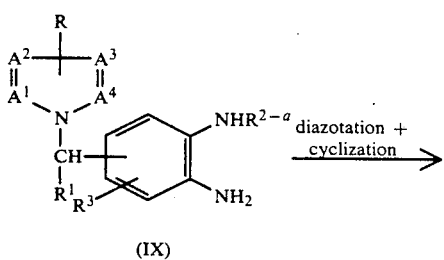

(IX)

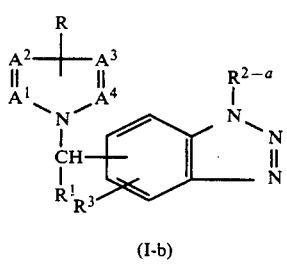

(I-b)

Said diazotative cyclization reaction can be carried out by stirring the diamine of formula (IX) in an acidic nitrite solution. Preferably the said reaction is conducted with an aqueous solution of nitrous acid or of a nitrite salt, e.g., sodium nitrite in the presence of a suitable acid such as, for example, hydrochloric acid, hydrobromic acid, formic acid, acetic acid, propanoic acid and the like acids, at a low temperature.

The compounds of formula (I), wherein $R^2$ is hydroxy, said compounds being represented by formula (I-c-1), can be prepared by cyclizing an appropriately substituted azole of formula (X), which in situ may be formed by reacting an intermediate of formula (XI) with hydrazine (XII) or a hydrate thereof.

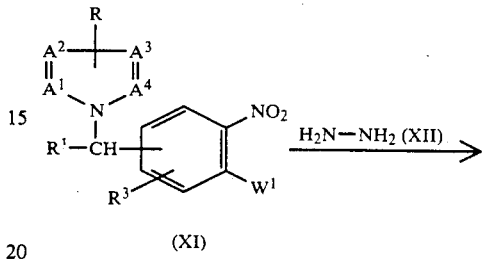

(XI)

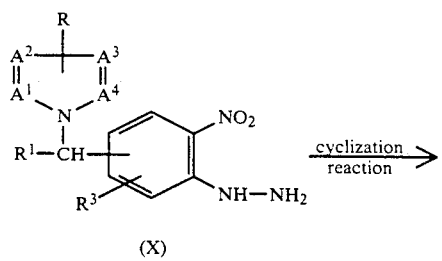

(X)

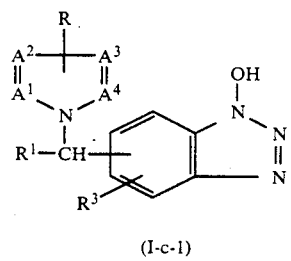

(I-c-1)

In (XI) $W^1$ represents an appropriate leaving group such as, for example, halo, preferably fluoro, chloro or bromo, a sulfonyloxy group, e.g., methylsulfonyloxy or 4-methylbenzenesulfonyloxy, or a $C_{1-6}$alkyloxy or $C_{1-6}$alkylthio group. The cyclization reaction may be carried out by stirring an intermediate of formula (XI) with hydrazine in a suitable reaction-inert solvent such as, for example, an alcohol, e.g., methanol, ethanol, 2-propanol, 1-butanol and the like or an aromatic hydrocarbon, e.g., benzene, methylbenzene, dimethylbenzene and the like. Somewhat elevated temperatures may be appropriate to enhance the rate of the reaction and preferably the reaction is carried out at the reflux temperature of the reaction mixture. After completion, the reaction mixture is preferably cooled and acidified with an acidic solution such as, for example, a hydrochloric acid solution.

The compounds of formula (I-c-1) can further be O-alkylated with a reagent of formula (XIII) following art-known procedures, thus preparing the corresponding compounds of formula (I-c-2) wherein $R^2$ is optionally substituted $C_{1-10}$alkyloxy, optionally substituted $C_{2-6}$alkenyloxy, $C_{2-6}$alkynyloxy, pyrimidinyloxy, di-($Ar^2$) methoxy or (1-$C_{1-4}$alkyl-4-piperidinyl)oxy, the said radical being represented by O-$R^{2-b}$.

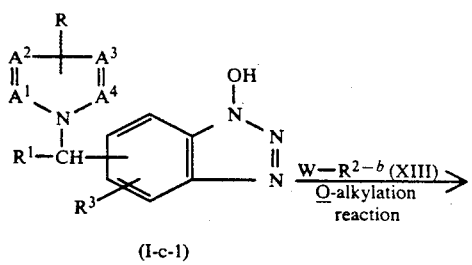

(I-c-1)

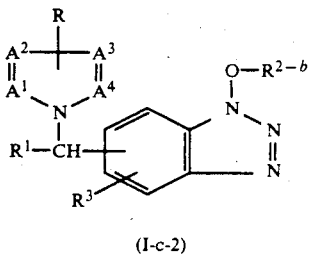

(I-c-2)

Said O-alkylation is conveniently conducted in a suitable reaction-inert solvent or a mixture of such solvents. Suitable reaction-inert solvents are, for example, an aromatic hydrocarbon, e.g., benzene, methylbenzene, dimethylbenzene, and the like; a lower alkanol, e.g., methanol, ethanol, 1-butanol and the like; a polar aprotic solvent, e.g., N,-N-dimethylformamide, N,-N-dimethylacetamide, hexamethylphosphoric triamide, dimethyl sulfoxide; and the like. Preferably in the presence of an appropriate base such as, for example, an alkali or an earth alkaline metal hydride, alkoxide, hydroxide, hydrogen carbonate, carbonate or amide. It may be advantageous previously to convert (I-c-1) into a metal salt form thereof, preferably the sodium salt, in the usual manner, e.g., by the reaction of (I-c-1) with a metal base such as sodium hydroxide and the like, and thereafter to use said metal salt in the reaction with (XIII).

The compounds of formula (I-b) may alternatively be prepared by reducing a compound of formula (I-c-1), thus preparing a compound of formula (I-b) wherein $R^2$ is hydrogen and, if further desired, reacting the thus obtained compound of formula (I-b-1) with a reagent $R^{2-c}W$ (XIV), thus preparing compounds of formula (I-b-2).

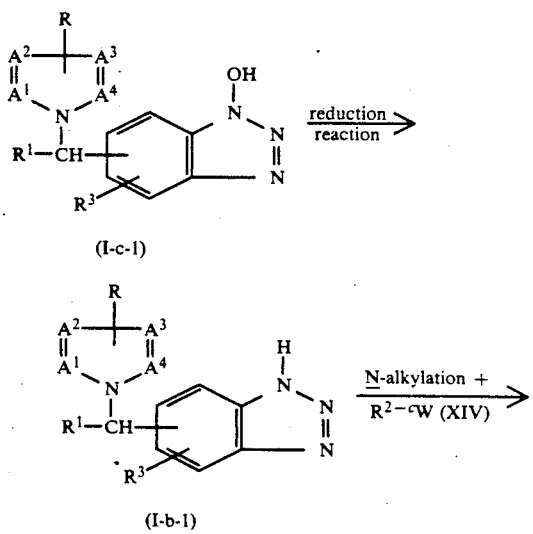

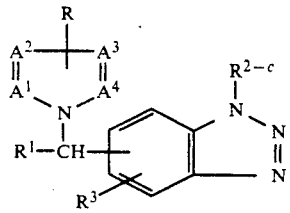

(I-b-2)

In (XIV) W has the previously defined meanings and $R^{2-c}$ has the previously defined meaning of $R^{2-a}$, provided that it is not hydrogen. Said reduction reaction may for example be conducted by contacting the compounds of formula (I-c-1) with hydrogen in the presence of an appropriate catalyst such as, for example, Raney-nickel, platinum, palladium, platinum(IV) oxide, and the like, in the presence of a reaction-inert organic solvent such as, a lower alkanol, e.g. methanol, ethanol and the like. Said reduction may alternatively be conducted by reacting the starting material (I-c-1) with titanium-(III) chloride or tin(II) chloride in hydrochloric acid, optionally in the presence of a reaction inert solvent. Preferably said reduction is carried out by O-alkylating (I-c-1) with a readily oxidizeable group such as, for example, $C_{1-6}$alkyloxycarbonylmethyl and the like groups and stirring the thus obtained intermediates in a suitable organic solvent, e.g., dimethyl sulfoxide, N,N-dimethylformamide and the like in the presence of a base such as, for example, an alkali or an earth alkaline metal carbonate, hydrogen carbonate, hydroxide, alkoxide or amide.

The N-alkylation reaction of (I-b-1) with (XIV) can be carried out in the usual manner, e.g., by stirring the reactants preferably at somewhat elevated temperatures in an appropriate organic solvent such as, for example, a polar aprotic solvent, e.g., dimethyl sulfoxide, dimethylformamide and the like in the presence of an appropriate base such as, for example, an alkali metal hydride, hydroxide, carbonate or amide.

The compounds of formula (I-a-1) can also be obtained by desulfurating an intermediate of formula (XV) in the usual manner, e.g., by treating the latter with Raney-nickel in the presence of an alcohol, e.g., ethanol or by treating the starting compounds with sodium nitrite in the presence of nitric acid in an aqueous medium.

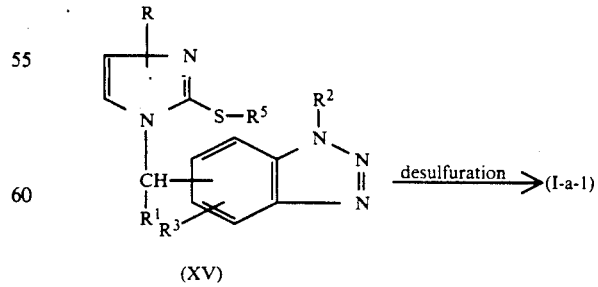

(XV)

$R^5$ in (XV) is $C_{1-6}$alkyl.

The compounds of formula (I) may also be converted into each other following art-known functional group transformation procedures. A number of such procedures will be described hereinafter in more detail.

The compounds of formula (I) containing an ester group may be converted into the corresponding acids following art-known saponification procedures, e.g., by treating the starting compound with an aqueous alkaline or an aqueous acidic solution. Vice versa, the carboxylic acid group may be converted into the corresponding ester group following art-known esterification procedures. For example, the carboxylic acid may be converted into a reactive derivative which subsequently is reacted with the corresponding alkanol; or by reacting the carboxylic acid and the alkanol with a suitable reagent capable of forming esters, e.g., dicyclohexylcarbodiimide, 2-chloro-1-methylpyridinium iodide and the like.

Compounds of formula (I) containing a formyl group may be converted into the corresponding oxime following art-known procedures, e.g., by treating the starting compound with hydroxylamine or an acid addition salt form thereof in a suitable solvent, e.g., water, a lower alkanol, an ether, in the presence of a base, e.g., an alkali metal hydroxide, carbonate or hydrogen carbonate.

Compounds of formula (I) containing an alkynyl group may be converted into the corresponding compounds having an alkenyl group by catalytically hydrogenating the starting compound in a suitable reaction-inert solvent according to art-known catalytic hydrogenation procedures. Suitable catalysts are for example palladium-on-charcoal, platinum-on-charcoal and the like.

Compounds of formula (I) wherein $R^3$ is hydrogen may by converted into compounds wherein $R^3$ is nitro by stirring the starting compound in a solution of nitrous acid in the presence of an appropriate acid, e.g., sulfuric acid, or a mixture of acetic acid and acetic acid anhydride.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) containing an acidic proton may also be converted to their therapeutically active non-toxic metal or amine substitution salts, by treatment with appropriate organic or inorganic bases. Conversely the metal or amine substitution salt form can be converted into the free acidic form by treatment with an acid.

A number of intermediates and starting materials in the foregoing preparation are known compounds which may be prepared according to art-known methodologies of preparing said or similar compounds and some intermediates are news. A number of such preparation methods will be described hereinafter in more detail.

Starting materials of formula (II) can conveniently be prepared by the following reaction sequence. An aldehyde or ketone of formula (XVI) is reduced with an appropriate reductant such as, for example an aluminum or boron hydride or a complex hydride, e.g., lithium aluminum hydride, sodium borohydride, yielding an alcohol of formula (XVII), and is subsequently converted into a benzotriazole of formula (VI-c-1) following the cyclization procedure described hereinabove for the conversion of (XI) to (I-c-1). If desired, the thus obtained benzotriazole may further be converted into an appropriate intermediate of formula (VI-c-2), (VI-b-1) or (VI-b-2) following the same procedures as described for the conversion of (I-c-1) to (I-c-2), (I-c-1) to (I-b-1) and (I-b-1) to (I-b-2). The desired starting materials of formula (II) wherein W represents a leaving group may then be obtained by converting the hydroxy moiety of the benzotriazoles of formulae (VI) into a reactive ester following standard procedures as known in the art. Halides are generally prepared by the reaction of (VI) with an appropriate halogenating agent such as, for example, thionyl chloride, sulfuryl chloride, pentachlorophoshorane, pentabromophoshorane, phosphoryl chloride, hydrochloric acid, hydrobromic acid and the like. When the leaving group is a iodide it is preferably prepared from the corresponding chloride or bromide by the replacement of that halogen with iodine. Other reactive esters such as methanesulfonates and 4-methylbenzenesulfonates are obtained by the reaction of the alcohol with an appropriate sulfonyl halide such as, for example, methanesulfonyl chloride and 4-methylbenzenesulfonyl chloride.

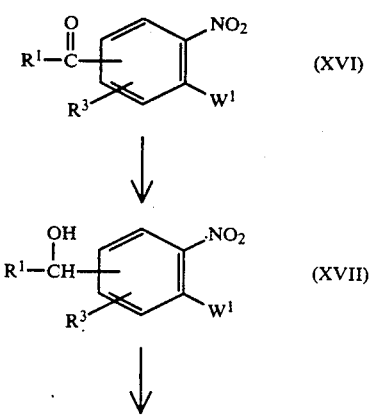

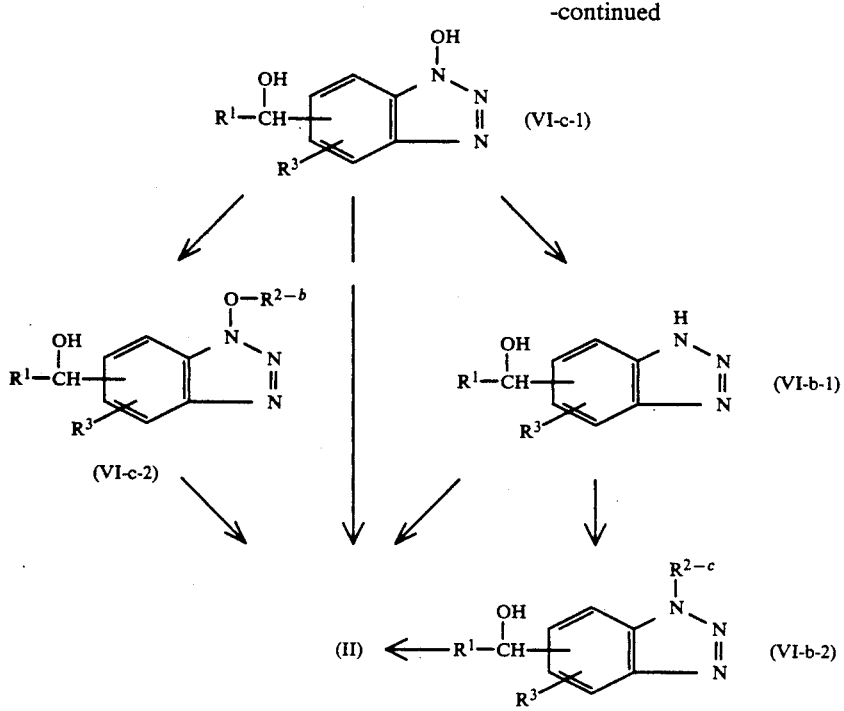

In the above reaction scheme $R^1$, $R^{2-b}$ and $R^{2-c}$ are the same as previously described.

In addition to the above described procedure the intermediates of formula (II), wherein $R^2$ is a radical of formula $R^{2-a}$, may also be prepared from an appropriately substituted benzoic acid of formula (XVIII) according to the following reaction sequence. An intermediate of formula (XVIII) is reacted with an appropriate amine of formula (XIX) following art-known N-arylation procedures and is subsequently subjected to a nitro-to-amine reduction reaction yielding an intermediate of formula (XXI). The latter is converted into a benzotriazole derivative of formula (XXII) according to similar cyclization procedures as described hereinabove for the preparation of (I-b). The carboxylic acid function of the benzotriazole (XXII) is then converted into the corresponding alcohol (VI-b-3) in the usual manner, e.g. by reduction with an appropriate reducing agent, e.g., lithium tetrahydroaluminate, in a suitable solvent, e.g. tetrahydrofuran. If further desired, an appropriate substituent $R^1$ may be introduced by converting the hydroxymethyl moiety of formula (VI-b-3) into a formyl moiety with a suitable oxidizing agent, e.g., manganese (IV) oxide or potassium permanganate, and reacting the thus obtained aldehyde (XXIII) with a metal alkyl, e.g., methyllithium, butyllithium, metal aryl, e.g., phenyllithium, or with a complex metal alkyl or aryl in a suitable solvent, e.g., tetrahydrofuran. The desired intermediates of formula (II-b) may then be obtained by converting the alcohol function of formula (VI-b-3) or (VI-b) into an appropriate leaving group following standard procedures described hereinabove.

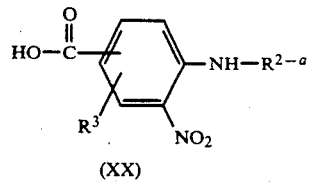
(XX)

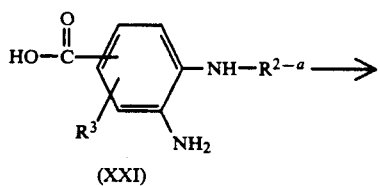
(XXI)

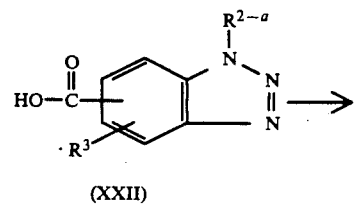
(XXII)

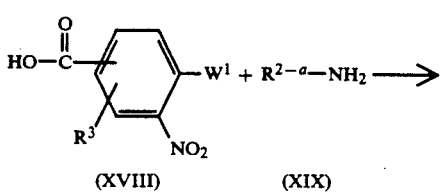
(XVIII)  (XIX)

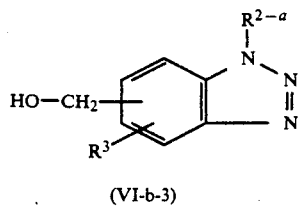
(VI-b-3)

-continued

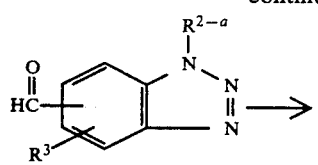

(XXIII)

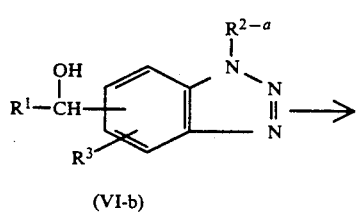

(VI-b)

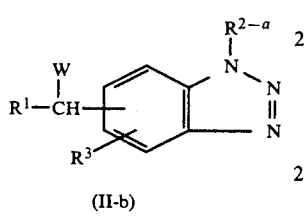

(II-b)

The intermediates of formula (IX) can be synthesized by various methodologies. For example, they may be prepared by the following sequence of reactions. An intermediate of formula (XVII) is converted into a reactive ester of formula (XXIV) and reacted with an 1H-azole of formula (III) following the same procedures as described hereinabove for the preparation of (I) starting from (II) and (III), yielding an intermediate of formula (XI). The latter is reacted with an appropriate amine of formula (XIX) following art-known N-arylation procedures and is subsequently subjected to a standard nitro-to-amine reduction reaction to yield the desired starting materials of formula (IX).

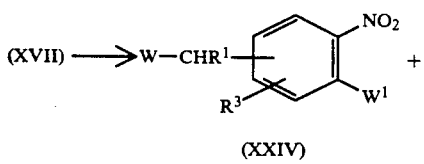

(XXIV)

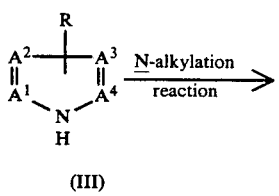

(III)

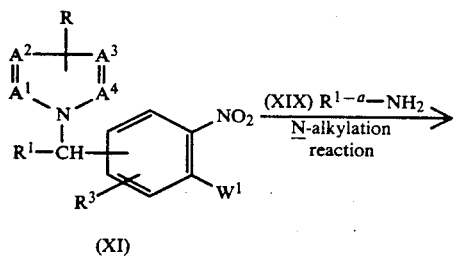

(XI)

-continued

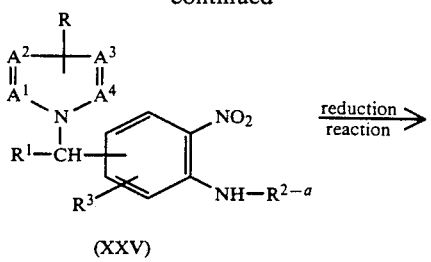

(XXV)

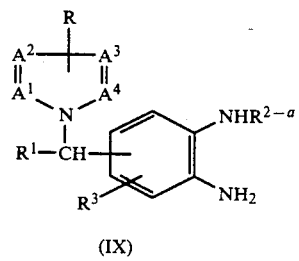

(IX)

In formula (XXIV) $W^1$ and W have the previously described meanings. The above mentioned nitro-to amine reduction reactions are generally carried out by stirring the starting compounds in a hydrogen containing medium in the presence of a suitable amount of an appropriate catalyst such as, for example, platinium-on-charcoal, palladium-on-charcoal, Raney-nickel and the like. In addition, the reduction may also be carried out by stirring the starting compound with sodium sulfide or sodium dithionite in a suitable solvent such as, for example water, methanol, ethanol and the like.

Intermediates of formula (XI) may also be prepared by nitration of a intermediate of formula (XXVI). The nitration reaction is conveniently conducted in a suitable solvent such as, for example, a halogenated hydrocarbon, e.g., trichloromethane and the like in the presence of an appropriate acid, such as, for example, sulfuric acid, or a mixture of acetic acid and acetic acid anhydride.

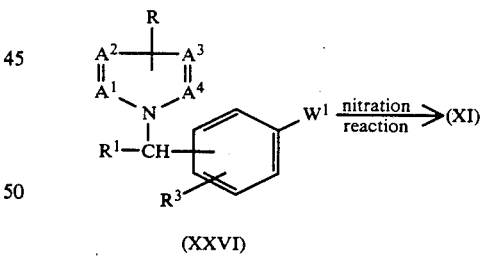

(XXVI)

Intermediates of formula (XV-a) can be prepared by stirring and heating an appropriate isothiocyanate (XXVIII), wherein $R^6$ is $C_{1-6}$alkyl or $Ar^2$—$C_{1-6}$alkyl, with an appropriately substituted amine (XXVII) in the presence of a suitable reaction-inert organic solvent such as, for example, a halogenated hydrocarbon, e.g., dichloromethane; subsequently by converting the thus obtained thiourea (XXIV) to the corresponding carbamimidothioate (XXXI) with a halogenide (XXX), wherein $R^5$ is $C_{1-6}$alkyl and Halo is preferably chloro, bromo or iodo, by stirring the reactants in the presence of an appropriate reaction-inert solvent, e.g., propanone; cyclizing the thus obtained carbamimidothioate (XXXI) by stirring and heating the latter in an aqueous acidic solvent, e.g., in aqueous sulfuric acid; and finally condensing the benzotriazole moiety following the cyclizing procedures described hereinabove.

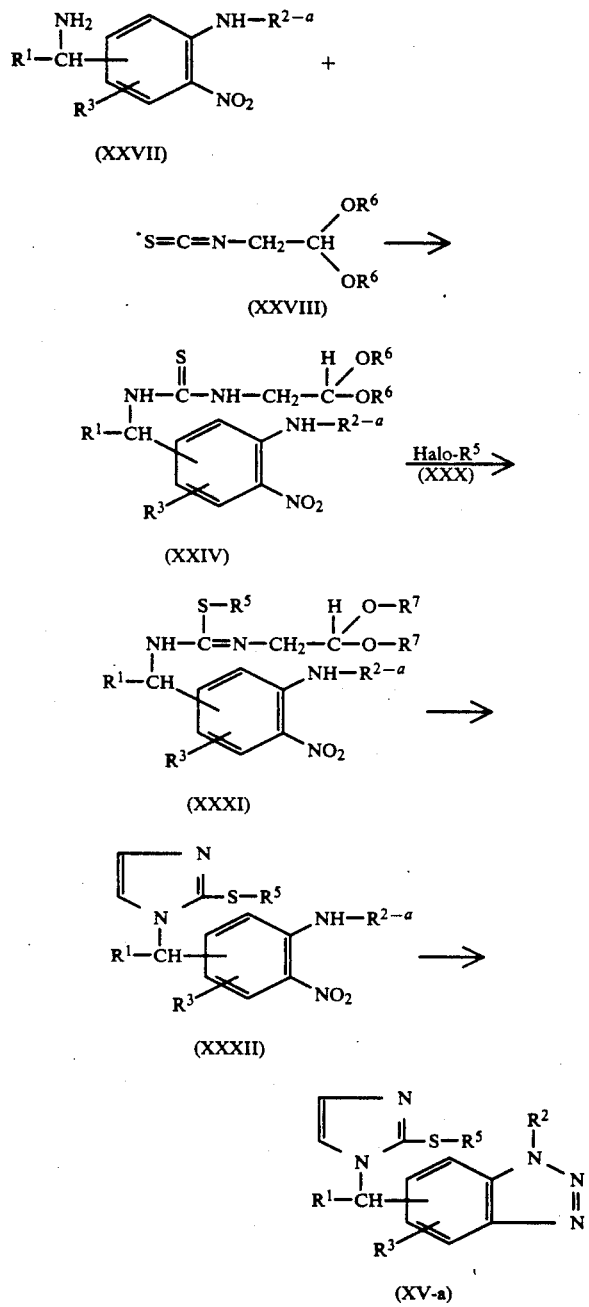

In all of the foregoing preparations, the reaction products may be isolated from the reaction mixture and, if necessary, further purified according to methodologies generally known in the art.

Starting materials and intermediates used in all of the preceding procedures for which no specific preparations are given herein, are generally known and/or may all be prepared following art-known methodologies described in the literature for the preparation of similar known compounds.

The compounds of formula (I) and some of the intermediates in this invention may have an asymmetric carbon atom in their structure. This chiral center may be present in a R— and a S—configuration, this R— and S—notation being in correspondence with the rules described by R. S. Cahn, C. Ingold and V. Prelog in Angew. Chem., Int. Ed. Engl., 5,385,511 (1966).

The compounds of formula (I) containing an alkene moiety may be present in a "E" or "Z" form, said E— and Z—notation having the meanings described in J. Org. Chem., 35, 2849–2868 (1970).

Pure stereochemically isomeric forms of the compounds of this invention may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids. They may also be derived from the corresponding pure stereochemically isomeric forms of the appropriate starting materials, provided that the reaction occurs stereospecifically.

The compounds of formula (I), the pharmaceutically acceptable acid-addition salts and possible stereochemically isomeric forms thereof have very interesting pharmacological properties. They inhibit the action of the enzyme aromatase which catalyses the formation of estrogens from androgenic steroids in mammals.

As generally accepted, estrogens are synthesized from androgens by the loss of the C-19 angular methyl group and the formation of the aromatic A ring. These reactions require NADPH and the enzyme aromatase. The inhibition of estrogen formation from androstenedione and testosterone can be demonstrated by in vitro-tests or in vivo-tests in mammals such as dogs, rats, mice and cats. The in vitro-inhibition of the aromatase activity can, for example, be demonstrated by analyzing the effects of the compounds of the present invention on the conversion of [1,2$^3$H]-androstenedione or [4$^{14}$C]-androstenedione into estrone and estradiol in the presence of human placental microsomes. The in vivo-inhibition of the aromatase activity can, for example, be demonstrated by measuring the suppression of the plasma estrogen concentration in female rats. The "In vitro-inhibition of the aromatase activity"-test and the "In vivo-inhibition of the aromatase activity"-test described hereinafter illustrate the estrogen inhibiting properties of the compounds of formula (I) and are based on the above principles.

In view of their capability to inhibit the biosynthesis of estrogens the subject compounds can be used in the treatment of estrogen dependent disorders such as, for example, breast cancer, endometriosis, endometrial cancer, polycystic ovarian disease, benign breast disease, gynecomastia, leyomyoma and the like.

The beneficial effect of aromatase inhibitors and/or anti estrogens in these disorders, especially in the treatment of breast cancer, is described in e.g. Cancer Research, 42, Suppl. 8: 3261s (1982).

The anti-tumour activity, especially in estrogen-dependent tumours, may in vivo be demonstrated, for example, by DMBA induced Mamma tumours in female Sprague-Dawley-rats.

In view of the usefulness of the subject compounds in the treatment of estrogen dependent disorders it is evident that the present invention provides a method of treating mammals suffering from said estrogen dependent disorders. Said method comprises the systemic administration to the latter of an amount, effective to treat estrogen dependent disorders, of a compound of formula (I), a pharmaceutically acceptable acid-addition salt, or a possible stereochemically isomeric form thereof. In particular there is provided a method of inhibiting estrogen synthesis in mammals which comprises the systemic administration to said mammals of an estrogen synthesis inhibitory amount, more particularly an aromatase inhibitory amount, of a compound of formula (I).

In addition to the above, some compounds of formula (I) show an inhibitory action or the biosynthesis of thromboxane $A_2$.

In view of their useful pharmacological properties, the subject compounds may be formulated into various pharmaceutical forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in treating the estrogen dependent disorders could easily determine the effective amount from the test results presented hereinafter. In general it is contemplated that an effective amount would be from 0.0001 mg/kg to 10 mg/kg body weight, and more preferably from 0.001 mg/kg to 0.5 mg/kg body weight.

The following examples are intended to illustrate and not to limit the scope of the invention. Unless otherwise stated all parts therein are by weight.

EXPERIMENTAL PART

A. Preparation of Intermediates

Example 1 a) A solution of 14 parts of (4-chloro-3-nitrophenyl) (4-fluorophenyl)-methanone in 69 parts of 2-propanamine was stirred overnight at reflux temperature. The reaction mixture was poured into water. The precipitate was filtered off and washed with water, dried, filtered and evaporated, yielding 14.7 parts (97.2%) of (4-fluorophenyl) [4-[(1-methylethyl)-amino]-3-nitrophenyl]methanone as a residue (int. 1).

b) A solution of 14.7 parts of (4-fluorophenyl) [4-[(1-methylethyl)-amino]-3-nitrophenyl]methanone in 120 parts of ethanol was hydrogenated at $2.10^5$Pa with 3 parts of Raney nickel catalyst. After the calculated amount of hydrogen was taken up, the catalyst was filtered off over diatomaceous earth and the filtrate was evaporated, yielding 12.3 parts (92.1%) of [3-amino-4-[(1-methylethyl)amino]phenyl] (4-fluorophenyl)-methanone as a residue (int. 2).

c) To a stirred and cooled (5° C.) solution of 12.3 parts of [3-amino-4-[(1-methylethyl)amino]phenyl] (4-fluorophenyl)methanone in 150 parts of a hydrochloric acid solution 6N were added 4.7 parts of sodium nitrite. Upon complete addition, stirring was continued for 1 hour at room temperature. The mixture was treated with a potassium carbonate solution to pH 9 and the product was extracted with dichloromethane. The extract was dried, filtered and evaporated, yielding 17 parts (100%) of (4-fluorophenyl) [1-methylethyl)-1H-benzotriazol-5-yl]methanone as a residue (int. 3).

d) To a stirred solution of 17 parts of (4fluorophenyl) [1-(1-methylethyl)-1H-benzotriazol-5-yl]methanone in 80 parts of ethanol were added 3.4 parts of sodium tetrahydroborate. After stirring for 1 hour at room temperature, the reaction mixture was neutralized to pH 7. The reaction mixture was concentrated and the product was extracted with ethyl acetate. The extract was dried, filtered and evaporated. The residue was purified by column chromatography over silica gel using a mixture of dichloromethane and methanol (98:2 by volume) as eluent. The pure fractions were collected and the eluent was evaporated, yielding 10.7 parts (62.5%) of α-(4-fluorophenyl)-1-(1-methylethyl)-1H-benzotriazole-5-methanol as a residue (int. 4).

In a similar manner there were also prepared: 1-cyclopropyl-α-(4-fluorophenyl)-1H-benzotriazole-5-methanol as a residue (int. 5); and 1-cyclohexyl-α-(4-fluorophenyl)-1H-benzotriazole-5-methanol as a residue (int. 6).

Example 2 a) A mixture of 50 parts of 4-chloro-3-nitrobenzoic acid and 222 parts of 1-butanamine was stirred for 3 hours at reflux temperature. After cooling and evaporation of the excess of 1-butanamine, the reaction mixture was acidified with a sulfuric acid solution 2N to pH 1. The precipitated product was filtered off and dried, yielding 59 parts (100%) of 4-(butylamino)-3-nitrobenzoic acid (int. 7).

b) A mixture of 50 parts of 4-(butylamino)-3-nitrobenzoic acid and 240 parts of methanol was hydrogenated in a Parr apparatus at 3.10⁵Pa and at room temperature with 40 parts of Raney Nickel catalyst under nitrogen atmosphere. After the calculated amount of hydrogen was taken up, the catalyst was filtered off over diatomaceous earth and the filtrate was evaporated to dry, yielding 43.7 parts (100%) of 3-amino-4-(butylamino)-benzoic acid; mp. 158° C. (int. 8).

c) To a stirred and cooled mixture of 43.7 parts of 3-amino-4-(butylamino)benzoic acid and 200 parts of a hydrochloric acid solution 6N was added dropwise a solution of 22 parts of sodium nitrite in a small amount of water. Upon complete addition, the reaction mixture was stirred for 4 hours at 10°-20° C. The product was filtered off, washed with 30 parts of water and crystallized from a mixture of 2-propanone and ethyl acetate. The product was filtered off and dried, yielding 33.3 parts (72.6%) of 1-butyl-1H-benzotriazole-5-carboxylic acid; mp. 192.5° C. (int. 9).

d) To a stirred and cooled (0° C.) suspension of 23.1 parts of lithium tetrahydroaluminate in 270 parts of dry tetrahydrofuran were added portionwise 45 parts of 1-butyl-1H-benzotriazole-5-carboxylic acid. Upon complete addition, stirring was continued for 1 hour at 0° C. The reaction mixture was hydrolysed with 50 parts of water. The whole was filtered and washed with a mixture of dichloromethane and methanol (90:10 by volume). The filtrate was evaporated to dry and the residue was purified by column chromatography over silica gel using a mixture of dichloromethane and methanol (98:2 by volume) as eluent. The pure fractions were collected and the eluent was evaporated, yielding 18 parts (42.7%) of 1-butyl-1H-benzotriazole-5-methanol as an oily residue (int. 10).

In a similar manner there were also prepared:

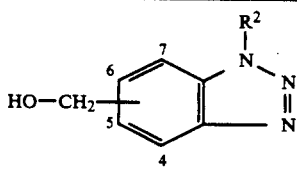

| Int. No. | R² | P | base/salt | mp (°C.) |
|---|---|---|---|---|
| 11 | —CH₃ | 7 | base | 106 |
| 12 | —(CH₂)₃—CH₃ | 7 | base | residue |
| 13 | —(CH₂)₃—CH₃ | 6 | base | residue |
| 14 | —CH₃ | 4 | base | residue |
| 15 | —CH₃ | 5 | base | residue |

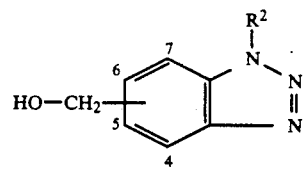

| Int. No. | R² | P | base/salt | mp (°C.) |
|---|---|---|---|---|
| 16 | —CH₃ | 6 | base | oil |
| 17 | —(CH₂)₃—CH₃ | 4 | base | residue |

In the foregoing and following tables of the experimental part "P" represents the position of the substitution on the benzene moiety of the benzotriazole heterocycle.

Example 3 a) To a stirred mixture of 7.4 parts of potassium permanganate, 0.6 parts of 2-(2-methoxyethoxy)-N,N-bis[2-(2-methoxyethoxy)ethyl] ethanamine and 130 parts of dichloromethane was added dropwise a solution of 7.6 parts of 1-methyl-1H-benzotriazole-7-methanol in dichloromethane. Upon complete addition, stirring was continued for 2 hours. The reaction mixture was filtered over diatomaceous earth and washed with dichloromethane. The organic layer was washed with 30 parts of a hydrochloric acid solution 2N and then with a sodium carbonate solution, dried, filtered and evaporated. The residue was purified by column chromatography over silica gel using a mixture of dichloromethane and methanol (98:2 by volume) as eluent. The pure fractions were collected and the eluent was evaporated, yielding 3.5 parts (46.6%) of 1-methyl-1-H-benzotriazole-7-carboxaldehyde; mp. 126° C. (int. 18).

b) To a stirred and refluxed Grignard complex, previously prepared starting from 8.15 parts of 1-bromo-3-fluorobenzene, 1.2 parts of magnesium and a small amount of 1,1'-oxybisethane was added a solution of 5 parts of 1-methyl-1H-benzotriazole-7-carboxaldehyde in 80 parts of 1,1'-oxybisethane. After stirring for 2 hours at room temperature, the reaction mixture was poured into 300 parts of water. The product was extracted three times with 65 parts of dichloromethane. The combined extracts were dried, filtered and evaporated. The residue was stirred for 15 minutes in 100 parts of water and 13 parts of petroleum ether at room temperature. The product was filtered off and dried, yielding 7.6 parts (95.2%) of α-(3-fluorophenyl)-1-methyl-1H-benzotriazole-7-methanol; mp. 152° C. (int. 19).

In a similar manner there were also prepared:

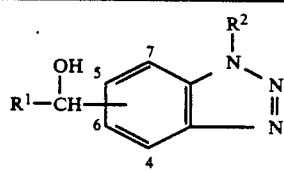

| Int. No. | R¹ | R² | P | base/salt | mp (°C.) |
|---|---|---|---|---|---|
| 20 | phenyl | —(CH₂)₃—CH₃ | 7 | base | 125° C. |
| 21 | phenyl | —CH₃ | 7 | base | residue |
| 22 | H₃C— | —CH₃ | 7 | base | 126° C. |
| 23 | H₃C— | —(CH₂)₃—CH₃ | 7 | base | residue |
| 24 | 3-Cl—C₆H₄— | —(CH₂)₃—CH₃ | 7 | base | 112.0° C. |

-continued

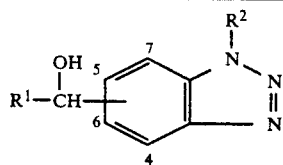

| Int. No. | R¹ | R² | P | base/salt | mp (°C.) |
|---|---|---|---|---|---|
| 25 | 4-Cl—C₆H₄— | —(CH₂)₃—CH₃ | 6 | base | residue |
| 26 | 4-F—C₆H₄— | —(CH₂)₃—CH₃ | 6 | base | residue |
| 27 | 3-F—C₆H₄— | —(CH₂)₃—CH₃ | 6 | base | residue |
| 28 | 3-F—C₆H₄— | —(CH₂)₃—CH₃ | 7 | base | 116° C. |
| 29 | 3-Cl—C₆H₄— | —CH₃ | 7 | base | 128° C. |
| 30 | 3-Cl—C₆H₄— | —(CH₂)₃—CH₃ | 6 | base | residue |
| 31 | 3-F—C₆H₄— | —CH₃ | 5 | base | residue |
| 32 | CH₃—(CH₂)₂— | —CH₃ | 5 | base | residue |
| 33 | 3-Cl—C₆H₄— | —CH₃ | 5 | base | residue |
| 34 | 3-Cl—C₆H₄— | —CH₃ | 6 | base | residue |
| 35 | 4-F—C₆H₄— | —CH₃ | 6 | base | residue |
| 36 | 4-Cl—C₆H₄— | —CH₃ | 6 | base | residue |
| 37 | CH₃—(CH₂)₂— | —CH₃ | 6 | base | residue |
| 38 | 3-Br—C₆H₄— | —CH₃ | 5 | base | oil |
| 39 | 3-F—C₆H₄— | —CH₃ | 6 | base | residue |
| 40 | 3-Cl—C₆H₄— | —(CH₂)₃—CH₃ | 5 | base | residue |
| 41 | H₃C— | —(CH₂)₃—CH₃ | 5 | base | residue |
| 42 | H₃C— | —CH₃ | 6 | base | residue |
| 43 | 3-F—C₆H₄— | —(CH₂)₃—CH₃ | 5 | base | residue |
| 44 | 4-F—C₆H₄— | —(CH₂)₃—CH₃ | 5 | base | 82° C. |
| 45 | 4-Cl—C₆H₄— | —(CH₂)₃—CH₃ | 5 | base | residue |
| 46 | 4-Br—C₆H₄— | —(CH₂)₃—CH₃ | 5 | base | residue |
| 47 | 4-Cl—C₆H₄— | —CH₃ | 5 | base | residue |
| 48 | 3-Br—C₆H₄— | —CH₃ | 6 | base | residue |
| 49 | 4-Br—C₆H₄— | —CH₃ | 6 | base | residue |
| 50 | 4-Br—C₆H₄— | —CH₃ | 5 | base | residue |
| 51 | 4-CF₃—C₆H₄— | —CH₃ | 6 | base | residue |
| 52 | 2-Cl—C₆H₄— | —CH₃ | 6 | base | residue |
| 53 | 4-CH₃—C₆H₄— | —CH₃ | 6 | base | residue |
| 54 | 2-naphthalenyl | —CH₃ | 6 | base | residue |
| 55 | 4-H₃CO—C₆H₄— | —CH₃ | 6 | base | residue | and α-[4-(4,5-dihydro-4,4-dimethyl-2-oxoazoly)-phenyl]-1-methyl-1H-benzotriazole-6-methanol as a residue (int. 56).

Example 4 a) A mixture of 36.5 parts of 1-butyl-1H-benzotriazole-5-methanol, 35 parts of manganese(IV) oxide and 390 parts of dichloromethane was stirred for 12 hours at room temperature. The manganese(IV) oxide was filtered off over diatomaceous earth and another portion of 35 parts of manganese(IV) oxide was added to the filtrate. After stirring for 12 hours at room temperature, the whole was filtered and the filtrate was evaporated. The residue was purified by column chromatography over silica gel using dichloromethane as eluent. The pure fractions were collected and the eluent was evaporated, yielding 15.3 parts (42.2%) of 1-butyl-1H-benzotriazole-5-carboxaldehyde as a residue (int. 57).

b) To a stirred and cooled (−78° C.) solution of 7.2 parts of 3-bromothiophene in 70 parts of 1,1′-oxybisethane were added 30 parts of a 1-butyllithium solution 1.6M in hexane. After stirring for 20 minutes at this low temperature, a solution of 6 parts of butyl-1H-benzotriazole-5-carboxaldehyde was added to the previous mixture. The reaction mixture was stirred for 2 hours at −78 ~ −40° C. The whole was poured into 200 parts of ice water and the product was extracted three times with 56 parts of 1,1′-oxybisethane. The combined extracts were dried, filtered and evaporated. The residue was purified by column chromatography over silica gel using a mixture of dichloromethane and methanol (98.2 by volume) as eluent. The pure fractions were collected and the eluent was evaporated. The residue was crystallized from 2,2′-oxybispropane. The product was filtered off and dried, yielding 5 parts (58.9%) of 1-butyl-α-(3-thienyl)-1H-benzotriazole-5-methanol; mp. 80° C. (int. 58).

In a similar manner there were also prepared:
1-butyl-α-(2-thienyl)-1H-benzotriazole-5-methanol as a residue (int. 59);

1-methyl-α-(2-thienyl)-1H-benzotriazole-6-methanol as a residue (int. 60); and 1-methyl-α-(3-thienyl)-1H-benzotriazole-6-methanol as a residue (int. 61).

Example 5 a) To a stirred mixture of 496 parts of aluminum chloride in 900 parts of benzene was added dropwise a solution of 256 parts of 4-fluoro-3-nitrobenzoyl chloride in 225 parts of benzene at ±10° C. Upon complete addition, stirring was continued first for 1.5 hours in an ice bath and then for 8 hours at room temperature. The mixture was heated to 60° C., cooled again and poured into crushed ice and 180 parts of concentrated hydrochloric acid. The separated organic layer was dried, filtered and concentrated. The concentrate was dissolved in 2100 parts of 2,2′-oxybispropane, the solution was treated with diatomaceous earth and activated charcoal. After filtration, the filtrate was concentrated. The crystallized product was filtered off and dried, yielding 223 parts (73%) of (4-fluoro-3-nitrophenyl) phenylmethanone; mp. 59° C. (int. 62).

b) To a cooled (ice bath) solution of 24.5 parts of (4-fluoro-3-nitrophenyl) phenylmethanone in 120 parts of methanol were added portionwise 1.5 parts of sodium tetrahydroborate. Upon complete addition, stirring was continued for 15 minutes at 0° C. A solution of 3 parts of acetic acid in 25 parts of water was added dropwise to the mixture. Upon completion, the mixture was concentrated. Water was added to the residue and the product was extracted with dichloromethane. The extract was dried, filtered and concentrated, yielding 25.1 parts (100%) of 4-fluoro-3-nitro-α-phenylbenzenemethanol as an oily residue (int. 63).

c) A mixture of 25 parts of 4-fluoro-3-nitro-α-phenylbenzenemethanol, 20 parts of hydrazine monohydrate and 80 parts of ethanol was stirred for 1.5 hours at reflux temperature. After cooling, 20 parts of a hydrochloric acid solution 10N were added. After concentration, the residue was washed twice with 50 parts of water and dissolved in a solution of 300 parts methanol (10%) in trichloromethane. The organic layer was dried, filtered and concentrated, yielding 23.8 parts (98.6%) of 1-hydroxy-α-phenyl-1H-benzotriazole-6-methanol as a residue (int. 64).

d) To a stirred solution of 1.2 parts of sodium hydroxide in 40 parts of methanol were added 7.8 parts of 1-hydroxy-α-phenyl-1H-benzotriazole-6-methanol. After concentration, 18 parts of methylbenzene were added to the concentrate. The solvent was evaporated again and the residue was dissolved in 27 parts of N,N-dimethylformamide. 5.52 Parts of 1-iodobutane were added at once and the whole was stirred for 30 minutes at 50° C. After concentration, 30 parts of water were added. The solidified product was filtered off, washed with water and dissolved in dichloromethane. The organic layer was dried, filtered and evaporated. The residue was crystallized from 17.5 parts of 2,2'-oxybispropane. The product was filtered off and dried, yielding 7.8 parts (87.4%) of 1-butoxy-α-phenyl-1H-benzotriazole-6-methanol; mp. 89.2° C. (int. 65).

In a similar manner there were also prepared:

1-ethoxy-α-phenyl-1H-benzotriazole-6-methanol; mp. 102.5° C. (int. 66);

1-(1-methylethoxy)-α-phenyl-1H-benzotriazole-6-methanol; mp. 109.6° C. (int. 67);

1-methoxy-α-phenyl-1H-benzotriazole-6-methanol; mp. 89.4° C.; and (int. 68)

α-phenyl-1-propoxy-1H-benzotriazole-6-methanol; mp. 104.1° C. (int. 69).

Example 6 a) To a stirred solution of 5.2 parts of 1-hydroxy-α-phenyl-1H-benzotriazole-6-methanol in 30 parts of dimethyl sulfoxide were added 0.96 parts of a sodium hydride dispersion 50%. The reaction mixture was stirred till no more hydrogen escapted. After the addition of 3.34 parts of ethyl 2-bromoacetate, the whole was stirred for 30 minutes at room temperature. 1.38 Parts of potassium carbonate were added and stirring was continued for 3 hours at 50° C. The dimethyl sulfoxide layer was evaporated and the residue was taken up in water and 20 parts of a hydrochloric acid solution 1N. The product was extracted with a mixture of trichloromethane and methanol (90:10 by volume). The extract was dried, filtered and concentrated. The concentrate was crystallized from 32.5 parts of dichloromethane. The product was filtered off and dried, yielding 3.1 parts (68.8%) of α-phenyl-1H-benzotriazole-5-methanol; mp. 143.0° C. (int. 70).

b) A mixture of 22.5 parts of α-phenyl-1H-benzotriazole-5-methanol, 4.8 parts of a sodium hydride dispersion 50% and 90 parts of N,N-dimethylformamide was stirred till hydrogen production had ceased. After the addition of 14.2 parts of iodomethane, stirring was continued for 30 minutes at room temperature. The mixture was concentrated. The concentrate was taken up in 50 parts of water and the product was extracted with dichloromethane. The extract was dried, filtered and concentrated. The concentrate was purified by filtration over silica gel using a mixture of trichloromethane and methanol (99:1 by volume) as eluent. The desired fraction was collected and the eluent was evaporated. The two isomers were separated by crystallization from ethyl acetate. The first isomer was further purified by crystallisation from ethyl acetate. The product was filtered off and dried, yielding 3 parts (12.5%) of 1-methyl-α-phenyl-1H-benzotriazole-6-methanol; mp. 145° C. (int. 71).

The other isomer was collected and crystallized three times from ethyl acetate. The product was filtered off and dried, yielding 3.3 parts (13.8%) of 1-methyl-α-phenyl-1H-benzotriazole-5-methanol; mp. 129° C. (int. 72)

Example 7

To a stirred solution of 6.5 parts of 1-butyl-α-(3-chlorophenyl)-1H-benzotriazole-6-methanol in 45 parts of tetrahydrofuran were added 3.7 parts of thionyl chloride at room temperature. After stirring for 1 hour, the reaction mixture was concentrated. The product was extracted with ethyl acetate. The extract was washed with a diluted sodium hydrogen carbonate solution, dried, filtered and evaporated, yielding 6.2 parts (88.3%) of 1-butyl-6-[chloro(3-chlorophenyl)methyl]-1H-benzotriazole as a residue (int. 73).

In a similar manner there were also prepared:

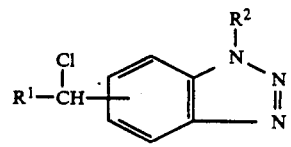

| Int. No. | $R^1$ | $R^2$ | P | base/salt | mp (°C.) |
|---|---|---|---|---|---|
| 74 | phenyl | —O—CH—(CH$_3$)$_2$ | 6 | HCl | oil |
| 75 | phenyl | —OCH$_3$ | 6 | HCl | residue |
| 76 | phenyl | —O—CH$_2$—CH$_3$ | 6 | HCl | residue |
| 77 | phenyl | —O—(CH$_2$)$_2$—CH$_3$ | 6 | HCl | oil |
| 78 | phenyl | —CH$_3$ | 6 | base | oil |
| 79 | phenyl | —O—(CH$_2$)$_3$—CH$_3$ | 6 | HCl | oil |
| 80 | phenyl | —CH$_3$ | 5 | base | oil |

-continued

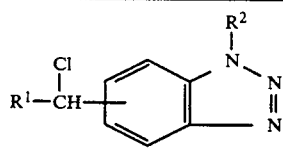

| Int. No. | R$^1$ | R$^2$ | P | base/salt | mp (°C.) |
|---|---|---|---|---|---|
| 81 | H— | —(CH$_2$)$_3$—CH$_3$ | 7 | base | residue |
| 82 | phenyl | —(CH$_2$)$_3$—CH$_3$ | 7 | base | residue |
| 83 | H— | —CH$_3$ | 7 | base | residue |
| 84 | phenyl | —CH$_3$ | 7 | base | residue |
| 85 | H$_3$C— | —CH$_3$ | 7 | base | residue |
| 86 | H$_3$C— | —(CH$_2$)$_3$—CH$_3$ | 7 | base | residue |
| 87 | 3-Cl—C$_6$H$_4$— | —(CH$_2$)$_3$—CH$_3$ | 7 | base | residue |
| 88 | 4-Cl—C$_6$H$_4$— | —(CH$_2$)$_3$—CH$_3$ | 6 | base | residue |
| 89 | H— | —CH$_3$ | 4 | base | residue |
| 90 | 4-F—C$_6$H$_4$— | —(CH$_2$)$_3$—CH$_3$ | 6 | base | residue |
| 91 | 3-F—C$_6$H$_4$— | —(CH$_2$)$_3$—CH$_3$ | 6 | base | residue |
| 92 | 3-F—C$_6$H$_4$— | —(CH$_2$)$_3$—CH$_3$ | 7 | base | residue |
| 93 | H$_3$C—(CH$_2$)$_2$— | —(CH$_2$)$_3$—CH$_3$ | 6 | base | oil |
| 94 | 3-F—C$_6$H$_4$— | —CH$_3$ | 7 | base | residue |
| 95 | 3-Cl—C$_6$H$_4$— | —CH$_3$ | 7 | base | residue |
| 96 | 3-F—C$_6$H$_4$— | —CH$_3$ | 5 | base | residue |
| 97 | H$_3$C—(CH$_2$)$_2$— | —CH$_3$ | 5 | base | residue |
| 98 | 3-Cl—C$_6$H$_4$— | —CH$_3$ | 5 | base | residue |
| 99 | 4-F—C$_6$H$_4$— | —CH$_3$ | 5 | base | residue |
| 100 | 3-Cl—C$_6$H$_4$— | —CH$_3$ | 6 | base | residue |
| 101 | 4-F—C$_6$H$_4$— | —CH$_3$ | 6 | base | residue |
| 102 | 4-Cl—C$_6$H$_4$— | —CH$_3$ | 6 | base | residue |
| 103 | H$_3$C—(CH$_2$)$_2$— | —CH$_3$ | 6 | base | residue |
| 104 | 3-Br—C$_6$H$_4$— | —CH$_3$ | 5 | base | residue |
| 105 | 3-F—C$_6$H$_4$— | —CH$_3$ | 6 | base | residue |
| 106 | 3-Cl—C$_6$H$_4$— | —(CH$_2$)$_3$—CH$_3$ | 5 | base | residue |
| 107 | H$_3$C— | —(CH$_2$)$_3$—CH$_3$ | 5 | base | residue |
| 108 | H$_3$C— | —CH$_3$ | 6 | base | residue |
| 109 | 3-F—C$_6$H$_4$— | —(CH$_2$)$_3$—CH$_3$ | 5 | base | residue |
| 110 | 4-F—C$_6$H$_4$— | —(CH$_2$)$_3$—CH$_3$ | 5 | base | residue |
| 111 | H— | —(CH$_2$)$_3$—CH$_3$ | 4 | base | residue |
| 112 | 4-Cl—C$_6$H$_4$— | —(CH$_2$)$_3$—CH$_3$ | 5 | base | residue |
| 113 | 3-thienyl | —(CH$_2$)$_3$—CH$_3$ | 5 | base | residue |
| 114 | 4-Br—C$_6$H$_4$— | —(CH$_2$)$_3$—CH$_3$ | 5 | base | residue |
| 115 | 2-thienyl | —(CH$_2$)$_3$—CH$_3$ | 5 | base | residue |
| 116 | 4-Cl—C$_6$H$_4$— | —CH$_3$ | 5 | base | residue |
| 117 | 4-F—C$_6$H$_4$— | —CH—(CH$_3$)$_2$ | 5 | base | residue |
| 118 | 3-Br—C$_6$H$_4$— | —CH$_3$ | 6 | base | residue |
| 119 | 4-Br—C$_6$H$_4$— | —CH$_3$ | 6 | base | residue |
| 120 | 4-Br—C$_6$H$_4$— | —CH$_3$ | 5 | base | residue |
| 121 | 4-F—C$_6$H$_4$— | -cyclopropyl | 5 | base | residue |
| 122 | 4-F—C$_6$H$_4$— | -cyclohexyl | 5 | base | residue |
| 123 | 4-CF$_3$—C$_6$H$_4$— | —CH$_3$ | 6 | base | residue |
| 124 | 2-Cl—C$_6$H$_4$— | —CH$_3$ | 6 | base | residue |
| 125 | 4-CH$_3$—C$_6$H$_4$— | —CH$_3$ | 6 | base | residue |
| 126 | 2-naphthalenyl | —CH$_3$ | 6 | base | residue |
| 127 | 4-CH$_3$O—C$_6$H$_4$— | —CH$_3$ | 6 | base | residue | and 6-(bromophenylmethyl)-1-methyl-1H-benzotriazole monohydrobromide (int. 128); and 6-[chloro[4-(4,5-dihydro-4,4-dimethyl-2-oxazolyl)-phenyl]methyl]-1-methyl-1H-benzotriazole as a residue (int. 129).

Example 8

A mixture of 245 parts of α-(4-chlorophenyl)-1-methyl-1H-benzotriazole-6-methanol and 1500 parts of a hydrobromic acid solution in acetic acid was stirred for 2.5 hours at 40° C. The reaction mixture was evaporated at 60° C. and the residue was stirred in dichloromethane. After cooling to 10° C., the precipitated product was filtered off and dried, yielding 285 parts (76.6%) of 6-[bromo(4-chlorophenyl)methyl]-1-methyl-1H-benzotriazole monohydrobromide (int. 130).

Example 9 a) To a stirred and cooled solution of 58.1 parts of (4-chloro-3-nitrophenyl)phenylmethanone in 240 parts of methanol were added portionwise 4.4 parts of sodium tetrahydroborate. Upon complete addition, stirring was continued for 30 minutes at room temperature. The reaction mixture was evaporated. The residue was taken up in water and the product was extracted with dichloromethane. The extract was dried, filtered and evaporated, yielding 58 parts (99.9%) of 4-chloro-3-nitro-α-phenylbenzenemethanol as a residue (int. 131).

b) A mixture of 58 parts of 4-chloro-3-nitro-α-phenylbenzenemethanol and 450 parts of a hydrobromic acid solution 48% in water was stirred for 45 minutes at reflux temperature. After cooling, the product was extracted with dichloromethane. The extract was dried, filtered and evaporated, yielding 71.4 parts (99.3%) of 4-(bromophenylmethyl)-1-chloro-2-nitrobenzene as a residue (int. 132).

c) A mixture of 31.9 parts of 4-(bromophenylmethyl)-1-chloro-2-nitrobenzene, 49.3 parts of 4-methyl-1H-imidazole and 120 parts of acetonitrile was stirred for 24 hours at reflux temperature. The reaction mixture was concentrated and the concentrate was taken up in 150 parts of water. The product was extracted with dichloromethane. The extract was dried, filtered and evaporated. The residue was purified by column chromatography over silica gel using a mixture of trichloromethane, methanol and methanol, saturated with ammonia, (98:1:1 by volume) as eluent. The desired fractions were collected and the eluent was evaporated. The residue was converted into the ethanedioate salt in 80 parts of 2-propanol. The salt was filtered off, washed with 2-propanol and dried, yielding 22.8 parts (54.5%) of 1-[(4-chloro-3-nitrophenyl)phenylmethyl]-4-methyl-1H-imidazole ethanedioate(1:1); mp. 105° C. (int. 133).

In a similar manner there were also prepared:
1-[(4-chloro-3-nitrophenyl)methyl]-1H-imidazole; mp. 81.7° C. (int. 134);
1-[(3-chloro-4-nitrophenyl)phenylmethyl]-1H-imidazole (int. 135);
1-[(4-chloro-3-nitrophenyl)phenylmethyl]-1H-imidazole (int. 136);
1-[(4-chloro-3-nitrophenyl)methyl]-2-methyl-1H-imidazole; mp. 102° C. (int. 137);
1-[(4-chloro-3-nitrophenyl)phenylmethyl]-5-methyl-1H-imidazole; mp. 164° C. (int. 138);
1-[(3-chlorophenyl)(4-methoxy-3-nitrophenyl)methyl]-1H-imidazole as a residue (int. 139); and
1-[(3-chloro-4-nitrophenyl)(4-chlorophenyl)methyl]-1H-imidazole ethanedioate(1:1) (int. 140).

Example 10

To a stirred solution of 10 parts of 4-chloro-α-methyl-3-nitrobenzenemethanol in 90 patrs of tetrahydrofuran were added 8 parts of 1,1'-carbonylbis[1Himidazole]. After stirring for 4 hours at a reflux temperature, the tetrahydrofuran layer was evaporated. After the addition of 90 parts of methylbenzene, the reaction mixture was stirred for 75 hours at reflux. The reaction mixture was evaporated and the residue was taken up in water. The whole was treated with an ammonium hydroxide solution and the product was extracted with dichloromethane. The extract was dried, filtered and evaporated. The residue was purified by column chromatography over silica gel using a mixture of trichloromethane and methanol, saturated with ammonia, (95:5 by volume) as eluent. The first fraction was collected and the eluent was evaporated. The residue was crystallized from 84 parts of 1,1'-oxybisethane. The product was filtered off and dried, yeilding 4.2 parts (33.3%) of 1-[1-(4-chloro-3-nitrophenyl)ethyl]-1H-imidazole (int. 141).

Example 11

A mixture of 2.52 parts of 4H-1,2,4-triazol-4-amine, 8 parts of 4-chloro-3-nitrobenzenemethanol methanesulfonate(ester) and 40 parts of acetonitrile was stirred for 3 hours at reflux temperature. After cooling, the product was filtered off, washed with acetonitrile and dried, yielding 9.9 parts (94%) of 4-amino-1-[(4-chloro-3-nitrophenyl-methyl]-1,2,4-triazolium methanesulfonate; mp. 163.9° C. (int. 142).

b) To a stirred solution of 8.75 parts of 4-amino-1-[(4-chloro-3-nitrophenyl)methyl]-1,2,4-triazolium methanesulfonate in 85 parts of a hydrochloric acid solution 1N were added 7.15 parts of phosphinic acid 50%. After cooling in ice, a solution of 3.5 parts of sodium nitrite in 15 parts of water was added. The mixture was stirred for 2 hours at room temperature. An excess of concentrated ammonium hydroxide was added and stirring was continued for 15 minutes. The product was filtered off, washed with water, 2-propanol and 2,2'-oxybispropane and crystallized from 8 parts of 2-propanol. The product was filtered off and dried, yielding 5 parts (83.8%) of 1-[(4-chloro-3-nitrophenyl)methyl]-1H-1,2,4-triazole; mp. 98.9° C. (int. 143).

In a similar manner there was also prepared:
1-[(4-chloro-3-nitrophenyl)phenylmethyl]-1H-1,2,4-triazole as an oily residue (int. 144).

Example 12

To 184 parts of cold (10° C., ice bath) concentrated sulfuric acid were added portionwise 75 parts of 1-[(3-methoxyphenyl)methyl]-1H-imidazole mononitrate during 1 hour. Upon complete addition, stirring was continued for 30 minutes at 10° C. 15 Parts ofconcentrated nitric acid were added dropwise during 30 minutes at 15° C. Uponcompletion, the whole was stirred for 30 minutes at 10° C. The reaction mixture was poured into 1500 parts of crushed ice and the whole was treatedwith an ammonium hydroxide solution. The product was extracted with dichloromethane. The extract was dried, filtered and evaporated. The residue was purified by column chromatography over silica gel using a mixture of ethyl acetate, methanol and methanol, saturated with ammonia, (95:2.5:2.5 by volume) as eluent. The pure fractions were collected and the eluent was evaporated in vacuo. The residue was stirred in 45 parts of ethyl acetate. The precipitated product was filtered off, washed with 2,2'-oxybispropane and dried, yielding 28.2 parts (40.3%) of 1-[(3-methoxy-4-nitrophenyl)methyl]-1H-imidazole (int. 145).

Example 13

A mixture of 8 parts of 1-[(4-chloro-3-nitrophenyl)-methyl]-1H-imidazole and 42 parts of cyclohexanamine was stirred for 2 hours at reflux temperature. The mixture was evaporated and the residue was stirred in 2,2'-oxybispropane. The precipitated product was filtered off, washed with water and 2,2'-oxybispropane and purified by column chromatography over silica gel using a mixture of trichloromethane and methanol (90:10 by volume) as eluent. The pure fractions were collected and the eluent was evaporated. The residue was stirred in a mixture of 2,2'-oxybispropane and ethyl acetate. The product was filtered off, washed with ethyl acetate and 2,2'-oxybispropane and dried in vacuo at 60° C., yielding 9.5 parts (93.8%) of H -cyclohexyl-4-(1H-imidazol-1-ylmethyl)-b 2-nitrobenzenamine; mp. 121.1° C. (int. 146).

In a similar manner there were also prepared:

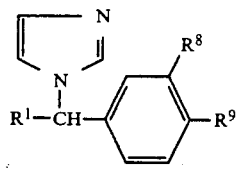

| Int. No. | R¹ | R⁸ | R⁹ | base/salt | mp (°C.) |
|---|---|---|---|---|---|
| 147 | H— | —NH—(CH₂)₃—CH₃ | —NO₂ | base | 117.5° C. |
| 148 | H— | —NO₂ | —NH—(CH₂)₃—CH₃ | base | 89.1° C. |
| 149 | H— | —NH-cyclohexyl | —NO₂ | base | 134.7° C. |
| 150 | H— | —NH—C₆H₅ | —NO₂ | base | 150.8° C. |
| 151 | H₃C— | —NO₂ | —NH—(CH₂)₅—CH₃ | HNO₃/H₂O | 84.7° C. |
| 152 | phenyl | —NO₂ | —NH—(CH₂)₃—CH₃ | base | residue |
| 153 | phenyl | —NH—(CH₂)₃—CH₃ | —NO₂ | base | oil |
| 154 | phenyl | —NH—CH—(CH₃)₂ | —NO₂ | base | oil |
| 155 | H— | —NH-cyclopropyl | —NO₂ | base | 111.6° C. |
| 156 | H— | —NH—CH—(CH₃)₂ | —NO₂ | base | 101.6° C. |
| 157 | H— | —NH—(CH₂)₂—CH₃ | —NO₂ | base | 98.9° C. |
| 158 | phenyl | —NH—CH₃ | —NO₂ | base | residue |
| 159 | H— | —NH—CH₂—(4-Cl—C₆H₄) | —NO₂ | base | 124.7° C. |
| 160 | H— | —NH—(CH₂)₂—CH(CH₃)₃ | —NO₂ | base | 75.4° C. |
| 161 | H— | —NO₂ | —NH—(CH₂)₂—CH₃ | base | 98.4° C. |
| 162 | H— | —NO₂ | —NH—CH—(CH₃)₂ | base | 98.3 |
| 163 | H— | —NO₂ | —NH—(CH₂)₂—C₆H₅ | base | 100.5 |
| 164 | H— | —NH—CH₂—(4-F—C₆H₄) | —NO₂ | base | 111.0 |
| 165 | H— | —NH—CH₂—CH₃ | —NO₂ | base | 106.2 |
| 166 | H— | —NH—CH₂—(3-F—C₆H₄) | —NO₂ | base | 95.4 |
| 167 | H— | —NH—CH—CH₂—CH₃<br>\|<br>CH₃ | —NO₂ | base | residue |
| 168 | H— | —NH-bicyclo[2.2.1]heptan-2-yl | —NO₂ | base | 130.7 |
| 169 | phenyl | —NH-cyclohexyl | —NO₂ | base | residue |
| 170 | H— | —NH-cyclopentyl | —NO₂ | base | 81.9 |
| 171 | H— | —NH-1,2,3,4-tetrahydro-1-naphthalenyl | —NO₂ | base | 118.0 |
| 172 | H— | —NH—CH₂—CH=CH₂ | —NO₂ | base | 86.4 |
| 173 | H— | —NO₂ | —NH—CH₂—C₆H₅ | base | residue |
| 174 | H— | —NH—CH₂-cyclopropyl | —NO₂ | base | 101.4 |
| 175 | H— | —NH—CH₂-2-thienyl | —NO₂ | base | residue |
| 176 | H— | —NH—(CH₂)₃—OH | —NO₂ | base | 107.0 |
| 177 | H— | —NH—CH₂—C—(CH₃)₃ | —NO₂ | base | 113.7 |
| 178 | H— | —NH—(CH₂)₂—N—(CH₃)₂ | —NO₂ | base | 111.6 |
| 179 | H— | —NH-2,3-dihydro-1H-inden-1-yl | —NO₂ | base | 200.2 |
| 180 | 4-Cl—C₆H₄— | —NH—CH—(CH₃)₂ | —NO₂ | (COOH)₂ | 110.9 |
| 181 | 4-Cl—C₆H₄— | —NH-cyclohexyl | —NO₂ | (COOH)₂ | 114.4 |
| 182 | 4-Cl—C₆H₄— | —NH-phenyl | —NO₂ | base | oil |
| 183 | 4-Cl—C₆H₄— | —NH—CH—C₆H₅<br>\|<br>CH₃ | —NO₂ | base | residue |
| 184 | 4-Cl—C₆H₄— | —NH—CH₂—(4-Cl—C₆H₄) | —NO₂ | base | residue |
| 185 | 4-Cl—C₆H₄— | —NH—CH₂—C₆H₅ | —NO₂ | base | residue |

Example 14

A mixture of 7.9 parts of N-cyclohexyl-4-(1H-imidazol-1-ylmethyl)-2-nitrobenzenamine, 22.9 parts of sodium dithionite, 288 parts of ethanol and 240 parts of water was stirred at room temperature. Upon complete reaction, the ethanol layer was evaporated. The aqueous layer was diluted with a potassium carbonate solution. The whole was extracted twice: first with dichloromethane and then with a mixture of trichloromethane and methanol (90:10 by volume). The combined extracts were dried, filtered and evaporated. The residue was taken up in methylbenzene and the solvent was evaporated again, yielding 7 parts (98.0%) of was evaporated again, yielding 7 parts (98.0%) of N¹-cyclohexyl-4-(1H-imidazol-1-ylmethyl)-1,2-benzenediamine as a residue (int. 186).

In a similar manner there were also prepared:

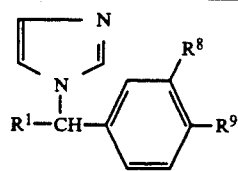

| Int. No. | R$^1$ | R$^8$ | R$^9$ | base/salt | mp (°C.) |
|---|---|---|---|---|---|
| 187 | —H | —NH$_2$ | —NH—CH$_3$ | base | residue |
| 188 | —H | —NH—(CH$_2$)$_3$—CH$_3$ | —NH$_2$ | base | residue |
| 189 | —H | —NH$_2$ | —NH—(CH$_2$)$_3$—CH$_3$ | base | residue |
| 190 | —H | —NH-cyclohexyl | —NH$_2$ | base | residue |
| 191 | —H | —NH—C$_6$H$_5$ | —NH$_2$ | base | residue |
| 192 | —H | —NH—CH$_2$—C$_6$H$_5$ | —NH$_2$ | base | residue |
| 193 | —C$_6$H$_5$ | —NH$_2$ | —NH—(CH$_2$)$_3$—CH$_3$ | base | residue |
| 194 | —CH$_3$ | —NH$_2$ | —NH—(CH$_2$)$_3$—CH$_3$ | base | residue |
| 195 | —C$_6$H$_5$ | —NH—(CH$_2$)$_3$—CH$_3$ | —NH$_2$ | base | residue |
| 196 | —C$_6$H$_5$ | —NH—CH(CH$_3$)$_2$ | —NH$_2$ | base | residue |
| 197 | —H | —NH-cyclopropyl | —NH$_2$ | base | residue |
| 198 | —H | —NH—CH(CH$_3$)$_2$ | —NH$_2$ | base | residue |
| 199 | —H | —NH$_2$ | —NH—CH$_2$—C$_6$H$_5$ | base | residue |
| 200 | —H | —NH—(CH$_2$)$_2$—CH$_3$ | —NH$_2$ | base | residue |
| 201 | —H | —NHCH$_2$—(4-Cl—C$_6$H$_4$) | —NH$_2$ | base | residue |
| 202 | —H | —NH(CH$_2$)$_2$—CH(CH$_3$)$_2$ | —NH$_2$ | base | residue |
| 203 | —H | —NH$_2$ | —NH—(CH$_2$)$_2$—C$_6$H$_5$ | base | residue |
| 204 | —H | —NH—CH$_2$(4-F—C$_6$H$_4$) | —NH$_2$ | base | residue |
| 205 | —H | —NH—CH$_2$—(3-F—C$_6$H$_4$) | —NH$_2$ | base | residue |
| 206 | —H | —NH—CH(CH$_3$)—CH$_2$—CH$_3$ | —NH$_2$ | base | residue |
| 207 | —H | —NH-bicyclo-[2.2.1]hept-2-yl | —NH$_2$ | base | residue |
| 208 | —H | —NH-cyclopentyl | —NH$_2$ | base | residue |
| 209 | —H | -1,2,3,4-tetrahydro-1-naphthalenyl | —NH$_2$ | base | residue |
| 210 | —H | —NH—CH$_2$—CH=CH$_2$ | —NH$_2$ | base | residue |
| 211 | —H | —NH—CH$_2$-c-C$_3$H$_5$ | —NH$_2$ | base | residue |
| 212 | —H | —NH—(CH$_2$)$_3$—OH | —NH$_2$ | base | residue |
| 213 | 4-Cl—C$_6$H$_4$— | (5-methyl-2-furanyl)-methylamino | —NH$_2$ | base | residue |
| 214 | 4-Cl—C$_6$H$_4$— | —NH—CH$_2$—(4-Cl—C$_6$H$_4$) | —NH$_2$ | base | residue |
| 215 | 4-Cl—C$_6$H$_4$— | —NH—C$_3$H$_5$-c | —NH$_2$ | base | residue |

Example 15

A mixture of 9 parts of 2,3-dihydro-N-[5(1H-imidazol-1-ylmethyl)-2-nitrophenyl]-1H-inden-1-amine, 2 parts of a solution of thiophene in methanol 4% and 200 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated, yielding 8 parts (97.3%) of N$^2$-(2,3-dihydro-1H-inden-1-yl)-4-(1H-imidazol-1-ylmethyl-1,2-benzenediamine as a residue (int. 216).

In a similar manner there were also prepared:

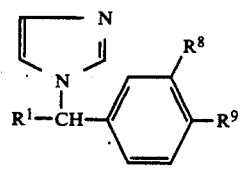

| Int. No. | R | R$^8$ | R$^9$ | base/salt | mp (°C.) |
|---|---|---|---|---|---|
| 217 | -phenyl | —NH—CH$_3$ | —NH$_2$ | base | residue |
| 218 | —H | —NH$_2$ | —NH—(CH$_2$)$_2$—CH$_3$ | base | residue |
| 219 | —H | —NH$_2$ | —NH—CH—(CH$_3$)$_2$ | base | residue |
| 220 | —H | —NH—CH$_2$—CH$_3$ | —NH$_2$ | base | residue |
| 221 | -phenyl | —NH-c-C$_6$H$_{11}$ | —NH$_2$ | base | residue |
| 222 | -phenyl | —NH$_2$ | —NH—CH$_2$—C$_6$H$_5$ | base | residue |
| 223 | —H | —NH—CH$_2$-2-thienyl | —NH$_2$ | base | residue |
| 224 | —H | —NH—CH$_2$—C—(CH$_3$)$_3$ | —NH$_2$ | base | residue |
| 225 | 4-Cl—C$_6$H$_4$— | —NH—CH—(CH$_3$)$_2$ | —NH$_2$ | base | residue |
| 226 | 4-Cl—C$_6$H$_4$— | —NH-c-C$_6$H$_{11}$ | —NH$_2$ | base | residue |
| 227 | —H | —NH(CH$_2$)$_2$—N(CH$_3$)$_2$ | —NH$_2$ | base | residue |

-continued

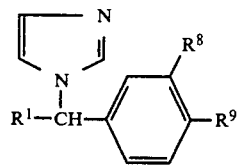

| Int. No. | R | R⁸ | R⁹ | base/salt | mp (°C.) |
|---|---|---|---|---|---|
| 228 | 4-Cl—C₆H₄— | —NH—C₆H₅ | —NH₂ | base | residue |
| 229 | 4-Cl—C₆H₄— | —NH(CH₂)₂—CH(CH₃)₂ | —NH₂ | base | residue |
| 230 | 4-Cl—C₆H₄— | —NH—CH(CH₃)—C₆H₅ | —NH₂ | base | residue |

Example 16

A solution of 10 parts of 6-[chloro[4-(4,5-dihydro-4,4-dimethyl-2-oxazolyl)phenyl]methyl]-1-methyl-1H-benzotriazole and 10 parts of 1H-imidazole in 80 parts of acetonitrile was stirred for 4 hours at reflux temperature. The reaction mixture was evaporated and the product was extracted with ethyl acetate. The extract was washed with a diluted potassium carbonate solution, dried, filtered and evaporated. The residue was purified by column chromatography over silica gel using a mixture of dichloromethane and methanol (98:2 by volume) as eluent. The pure fractions were collected and the eluent was evaporated, yielding 7.1 parts (65.6%) of 6-[[4-(4,5-dihydro-4,4-dimethyl-2-oxazolyl)-phenyl](1H-imidazol-1-yl)methyl]-1-methyl-1-methyl-1H-benzenotriazole as a residue (int. 231).

B. Preparation of Final compounds

Example 17

A mixture of 4 parts of 5-(chlorophenylmethyl)-1-methyl-1H-benzotriazole, 5.65 parts of 1H-imidazole and 20 parts of acetonitrile was stirred for 1.5 hours at reflux temperature. After concentration, 50 parts of water were added and the product was extracted with dichloromethane. The extract was dried, filtered and concentrated. The residue was purified by filtration over silica gel using a mixture of trichloromethane and methanol (95:5 by volume) as eluent. The pure fractions were collected and the eluent was evaporated. The residue was converted into the nitrate salt in 45 parts of tetrahydrofuran. The salt was filtered off, washed with tetrahydrofuran and dried, yielding 3.9 parts (80.2%) of 5-[(1H-imidazol-1-yl)phenylmethyl]-1-methyl-1H-benzotriazole mononitrate; mp. 111.9° C. (compound 1).

In a similar manner there were also prepared:

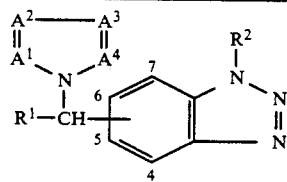

| Comp. No. | R¹ | R² | —A¹=A²—A³=A⁴— | P | base/salt | mp (°C.) |
|---|---|---|---|---|---|---|
| 2 | phenyl | —O—CH—(CH₃)₂ | —CH=CH—N=CH— | 6 | HNO₃ | 103.4 |
| 3 | phenyl | —O—CH₃ | —CH=CH—N=CH— | 6 | HNO₃ | 93.1 |
| 4 | phenyl | —O—CH₂—CH₃ | —CH=CH—N=CH— | 6 | HNO₃ | 98.1 |
| 5 | phenyl | —O—CH₂—CH₂—CH₃ | —CH=CH—N=CH— | 6 | HNO₃ | 120.2 |
| 6 | phenyl | —O—(CH₂)₃—CH₃ | —CH=CH—N=CH— | 6 | HNO₃ | 86.0 |
| 7 | phenyl | —CH₃ | —CH=CH—N=CH— | 6 | (COOH)₂ | 112.6 |
| 8 | H— | —(CH₂)₃—CH₃ | —CH=CH—N=CH— | 7 | base | 109.7 |
| 9 | phenyl | —(CH₂)₃—CH₃ | —CH=CH—N=CH— | 7 | HCl | 225.2 |
| 10 | H— | —CH₃ | —CH=CH—N=CH— | 7 | 0.5 H₂O | 175.8 |
| 11 | phenyl | —CH₃ | —CH=CH—N=CH— | 7 | base | 192.2 |
| 12 | H₃C— | —CH₃ | —CH=CH—N=CH— | 7 | base | 180.1 |
| 13 | H₃C— | —(CH₂)₃—CH₃ | —CH=CH—N=CH— | 7 | (COOH)₂ | 85.8 |
| 14 | 3-Cl—C₆H₄— | —(CH₂)₃—CH₃ | —CH=CH—N=CH— | 7 | (COOH)₂ | 144.3 |
| 15 | 4-Cl—C₆H₄— | —(CH₂)₃—CH₃ | —CH=CH—N=CH— | 6 | (COOH)₂ | 99.4 |
| 16 | H— | —CH₃ | —CH=CH—N=CH— | 4 | base | 132.7 |
| 17 | 4-F—C₆H₄— | —(CH₂)₃—CH₃ | —CH=CH—N=CH— | 6 | (COOH)₂ | 91.2 |
| 18 | 3-F—C₆H₅— | —(CH₂)₃—CH₃ | —CH=CH—N=CH— | 6 | (COOH)₂ | 89.8 |
| 19 | 3-F—C₆H₄— | —(CH₂)₃—CH₃ | —CH=CH—N=CH— | 7 | HCl | 212.0 |
| 20 | CH₃—(CH₂)₂— | —(CH₂)₃—CH₃ | —CH=CH—N=CH— | 6 | (COOH)₂ | 124.5 |
| 21 | 3-F—C₆H₄— | —CH₃ | —CH=CH—N=CH— | 7 | base | 182.3 |
| 22 | 3-Cl—C₆H₄— | —CH₃ | —CH=CH—N=CH— | 7 | base | 195.1 |
| 23 | 3-Cl—C₆H₄— | —(CH₂)₃—CH₃ | —CH=CH—N=CH— | 6 | (COOH)₂ | 71.5 |
| 24 | 3-F—C₆H₄— | —CH₃ | —CH=CH—N=CH— | 5 | base | 150.1 |
| 25 | CH₃—(CH₂)₂— | —CH₃ | —CH=CH—N=CH— | 5 | base | 112.4 |
| 26 | 3-Cl—C₆H₄— | —CH₃ | —CH=CH—N=CH— | 5 | base | 146.1 |

-continued

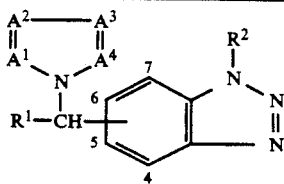

| Comp. No. | R¹ | R² | —A¹=A²—A³=A⁴— | P | base/salt | mp (°C.) |
|---|---|---|---|---|---|---|
| 27 | 4-F—C₆H₄— | —CH₃ | —CH=CH—N=CH— | 5 | (COOH)₂ | 152.4 |
| 28 | 3-Cl—C₆H₄— | —CH₃ | —CH=Ch—N—CH— | 6 | (COOH)₂ | 90.5 |
| 29 | 4-F—C₆H₄— | —CH₃ | —CH=CH—N=CH— | 6 | (COOH)₂ | 96.5 |
| 30 | 4-Cl—C₆H₄— | —CH₃ | —CH=CH—N=CH— | 6 | (COOH)₂/0.5 H₂O | 90.2 |
| 31 | H₃C—(CH₂)₂— | —CH₃ | —CH=CH—N=CH— | 6 | base | 95.0 |
| 32 | 3-Br—C₆H₄— | —CH₃ | —CH=CH—N=CH— | 5 | base | 143.2 |
| 33 | 3-F—C₆H₄— | —CH₃ | —CH=CH—N=CH— | 6 | (COOH)₂ | 189.9 |
| 34 | 3-Cl—C₆H₄— | —(CH₂)₃—CH₃ | —CH=CH—N=CH— | 5 | (COOH)₂ | 120.8 |
| 35 | H₃C— | —(CH₂)₃—CH₃ | —CH=CH—N=CH— | 5 | *(1:1) | 100.5 |
| 36 | H₃C— | —CH₃ | —CH=CH—N=CH— | 6 | base | 116.8 |
| 37 | 3-F—C₆H₄— | —(CH₂)₃—CH₃ | —CH=CH—N=CH— | 5 | (COOH)₂ | 131.2 |
| 38 | 4-F—C₆H₄— | —(CH₂)₃—CH₃ | —CH=CH—N=CH— | 5 | (COOH)₂ | 166.4 |
| 39 | H— | —(CH₂)₃—CH₃ | —CH=CH—N=CH— | 4 | (COOH)₂ | 95.8 |
| 40 | 4-Cl—C₆H₄— | —(CH₂)₃—CH₃ | —CH=CH—N=CH— | 5 | (COOH)₂/0.5 H₂O | 135.7 |
| 41 | 3-thienyl | —(CH₂)₃—CH₃ | —CH=CH—N=CH— | 5 | (COOH)₂ | 168.9 |
| 42 | 4-Br—C₆H₄— | —(CH₂)₃—CH₃ | —CH=CH—N=CH— | 5 | (COOH)₂/0.5 H₂O | 152.9 |
| 43 | 3-Cl—C₆H₄— | —CH₃ | —CH=CH—N=C—<br>       \|<br>      CH₃ | 6 | base | 177.4 |
| 44 | 2-thienyl | —(CH₂)₃—CH₃ | —CH=CH—N=CH— | 5 | (COOH)₂ | 143.5 |
| 45 | 4-Cl—C₆H₄— | —CH₃ | —N=CH—N=CH— | 6 | (COOH)₂ | 104.2 |
| 46 | 4-Cl—C₆H₄— | —CH₃ | —CH=N—N=CH— | 6 | 0.5 H₂O | 119.8 |
| 47 | 4-Cl—C₆H₄— | —CH₃ | —CH=CH—N=CH— | 5 | base | 172.4 |
| 48 | 4-Cl—C₆H₄— | —CH₃ | —CH=CH—N=CH— | 6 | HCl/H₂O | 151.2 |
| 49 | 4-F—C₆H₄— | —CH—(CH₃)₂ | —CH=CH—N=CH— | 5 | base | 155.3 |
| 50 | 3-Br—C₆H₄— | —CH₃ | —CH=CH—N=CH— | 6 | (COOH)₂/0.5 H₂O | 107.7 |
| 51 | 4-Br—C₆H₄— | —CH₃ | —CH=CH—N=CH— | 6 | (COOH)₂ | 136.2 |
| 52 | 4-Br—C₆H₄— | —CH₃ | —CH=CH—N=CH— | 5 | base | 180.1 |
| 53 | 4-F—C₆H₄— | c-C₃H₅— | —CH=CH—N=CH— | 5 | base | 94.6 |
| 54 | 4-F—C₆H₄— | c-C₆H₁₁— | —CH=CH—N=CH— | 5 | base | 157.6 |
| 55 | 4-CF₃—C₆H₄— | —CH₃ | —CH=CH—N=CH— | 6 | (COOH)₂/0.5 H₂O | 89.9 |
| 56 | 2-Cl—C₆H₄— | —CH₃ | —CH=CH—N=CH— | 6 | (COOH)₂/0.5 H₂O | 132.6 |
| 57 | 4-CH₃—C₆H₄— | —CH₃ | —CH=CH—N=CH— | 6 | (COOH)₂/0.5 H₂O | 140.9 |
| 58 | 2-naphthalenyl | —CH₃ | —CH=CH—N=CH— | 6 | 0.5 H₂O | 148.8 |
| 59 | 4-CH₃O—C₆H₄— | —CH₃ | —CH=CH—N=CH— | 6 | (COOH)₂ | 144.2 |
| 60 | C₆H₅—CH₂— | —CH₃ | —CH=CH—N=CH— | 5 | base | 159.9 |
| 61 | CN—C₆H₅— | —CH₃ | —CH=CH—N=CH— | 5 | base | 176.5 |

*(E)-2-butenedioate

Example 18

A mixture of 12.8 parts of 6-(bromophenylmethyl)-1-methyl-1H-benzotriazole monohydrobromide, 14.8 parts of 4-methyl-1H-imidazole and 80 parts of acetonitrile was stirred for 8 hours at reflux temperature. The mixture was concentrated and the residue was stirred in 100 parts of water. The product was extracted with dichloromethane. The extract was dried, filtered and evaporated. The residue was purified twice by column chromatography over silica gel using a mixture of trichloromethane and methanol (99:1 by volume) as eluent. The desired fraction was collected and the eluent was evaporated. The residue was purified by reversed phase chromatography (HPLC) over Li Chroprep RP 18 using a mixture of methanol, tetrahydrofuran and ammonium acetate (30:5:65 by volume) as eluent. The pure fraction was collected and the eluent was evaporated. The residue was converted into the ethanedioate salt in tetrahydrofuran. The salt was filtered off and dried, yielding 1.6 parts (13.5%) of 1-methyl-6-[(4-methyl-1H-imidazol-1-yl)phenylmethyl]-1H-benzo- triazole ethanedioate(1:1); mp. 203.1° C. (compound 62).

Example 19

A solution of 203 parts of 6-[bromo(4-chlorophenyl)-methyl]-1-methyl-1H-benzotriazole monohydrobromide and 170 parts of 1H-imidazole in 1350 parts of methylbenzene was stirred for 28 hours at reflux temperature. The reaction mixture was allowed to cool to 80° C. and then evaporated. The oily residue was dissolved in dichloromethane. The organic layer was washed with a diluted hydrochloric acid solution. The separated aqueous layer was treated with a sodium hydroxide solution and extracted with dichloromethane. The combined dichloromethane layers were washed with water, dried, filtered and evaporated. The residue was purified by column chromatography over silica gel using a mixture of dichloromethane and methanol (95:5 by volume) as eluent. The pure fractions were collected and the eluent was evaporated. To the residue were added 210 parts of 1,1'-oxybisethane and the whole was allowed to stand over weekend. The solid product was filtered off and dried at 50° C., yielding 48.1 parts (29.7%) of 6-[(4-chlorophenyl)(1H-imidazol-1-yl)methyl]1-methyl-1H-benzotriazole; mp. 87.7° C. (compound 63).

Example 20

To a stirred solution of 28.4 parts of 1H-1,2,4-triazole in 135 parts of N,N-dimethylformamide were added 11.4 parts of a sodium hydride dispersion 80% under nitrogen atmosphere. After stirring for 1 hour at room temperature, a solution of 40 parts of 6-[chloro(4-chlorophenyl)methyl]-1-methyl-1H-benzotriazole in 90 parts of N,N-dimethylformamide was added to the mixture. The whole was stirred for 1 hour at 60° C. The reaction mixture was diluted with 50 parts of water and the whole was evaporated. The residue was extracted with ethyl acetate. The extract was washed with water, dried, filtered and evaporated. The residue was purified by column chromatography over silica gel using a mixture of dichloromethane and methanol (99:1 by volume) as eluent. The pure fractions were collected and the eluent was evaporated. The residue was crystallized from a mixture of 2-propanone and 1,1'-oxybisethane. The product was filtered off and dried, yielding 13 parts (29.2%) of 6-[(4-chlorophenyl)-(1H-1,2,4-triazol-1-yl)methyl]-1-methyl-1H-benzotriazole; mp. 178.9° C. (compound 64).

Example 21

To a stirred solution of 4.25 parts of 1H-1,2,4-triazole in 47 parts of N,N-dimethylformamide were added 2 parts of a sodium hydride dispersion 50% under nitrogen atmosphere. The whole was stirred for 10 minutes at room temperature and a solution of 6 parts of 6-[chloro(3-chlorophenyl)methyl]-1-methyl-1H-benzotriazole in 47 parts of N,N-dimethylformamide was added to the mixture. The whole was stirred for 1 hour at 50° C. and then cooled to room temperature. The product was extracted with ethyl acetate. The extract was dried, filtered and evaporated. The residue was purified by column chromatography over silica gel using a mixture of dichloromethane and methanol (95:5 by volume) as eluent. The pure fractions were collected and the eluent was evaporated. The residue was converted into the ethanedioate salt in 2-propanone. The salt was filtered off and crystallized from a mixture of acetonitrile and 1,1'-oxybisethane. The product was filtered off and dried, yielding 2.8 parts (33.7%) of dried, yielding 2.8 parts (33.7%) of 6-[(3-chlorophenyl)(1H-1,2,4-triazol-1-yl)methyl]-1-methyl-1H-benzotriazole ethanedioate(1:1); mp. 125.0° C. (compound 65).

Example 22

A mixture of 9.1 parts of 6-(bromophenylmethyl)-1-methyl-1H-benzotriazole monohydrobromide, 10.25 parts of (4-methyl-1H-imidazol-1-yl)phenylmethanone and 64 parts of acetonitrile was stirred for 3 hours at reflux temperature. The acetonitrile layer was evaporated and the residue was stirred overnight at room temperature in a mixture of 16.6 parts of potassium carbonate and 80 parts of water. The product was extracted with dichloromethane. The extract was dried, filtered and evaporated. The residue was purified by column chromatography over silica gel using a mixture of trichloromethane and methanol (98:2 by volume) as eluent. The desired fraction was collected and the eluent was evaporated. The residue was purified by reversed phase chromatography (HPLC) over Li Chroprep RP 18 using a mixture of methanol, tetrahydrofuran and ammonium acetate (30:5:65 by volume) as eluent. The pure fraction was collected and the eluent was evaporated. The residue was further purified by column chromatography over silica gel using a mixture of trichloromethane and methanol (95:5 by volume) as eluent. The pure fractions were collected and the eluent was evaporated. The residue was converted into the ethanedioate salt in tetrahydrofuran. The salt was filtered off and dried in vacuo at 80° C., yielding 3.1 parts (35.8%) of 1-methyl-6-[(5-methyl-1H-imidazol-1-yl)phenylmethyl]-1H-benzotriazole ethanedioate (1:1); mp. 120.7° C. (compound 66).

EXAMPLE 23

A mixture of 8.2 parts of 6-(bromophenylmethyl)-1-methyl-1H-benzotriazole monohydrobromide, 3.45 parts of 4H-1,2,4-triazole-4-amine and 64 parts of acetonitrile was stirred first for 2 hours at reflux temperature and then overnight at room temperature. The precipitate was filtered off and the filtrate was concentrated, yielding 4-amino-1-[(1-methyl-1H-benzotriazol-6-yl)phenylmethyl]-4H-1,2,4-triazolium bromide. To a stirred solution of the latter, 7.3 parts of a phosphinic acid solution 50% and 7.3 parts of a hydrochloric acid solution 12N in 40 parts of methanol and 20 parts of water was added dropwise a solution of 3.45 parts of sodium nitrite in 20 parts of water. Upon complete addition, stirring was continued for 30 minutes at room temperature. The methanol layer was evaporated and the residue was treated with an ammonium hydroxide solution. The product was extracted with dichloromethane. The extract was dried, filtered and evaporated. The residue was purified twice by column chromatography over silica gel using a mixture of trichloromethane and methanol (98:2 by volume) as eluent. The pure fractions were collected and the eluent was evaporated. The residue was converted into the ethanedioate salt in 36 parts of tetrahydrofuran. The salt was filtered off and crystallized from 45 parts of ethyl acetate. The product was filtered off and dried, yielding 3.1 parts (40.7%) of 1-methyl-6-[phenyl-(1H-1,2,4-triazol-1-yl)methyl]-1H-benzotriazole ethanedioate(1:1); mp. 164.9° C. (compound 67).

Example 24

To a stirred and heated solution of 3.2 parts of 1-methyl-α-(2-thienyl)-1H-benzotriazole-6-methanol in 45 parts of tetrahydrofuran were added 4.2 parts of 1,1'-carbonylbis[1H-imidazole] under nitrogen atmosphere. After stirring for 30 minutes at 50° C., the reaction mixture was evaporated. The product was extracted with ethyl acetate. The extract was washed with a diluted sodium hydrogen carbonate solution, dried, filtered and evaporated. The residue was purified by column chromatography over silica gel using a mixture of dichloromethane and methanol (98:2 by volume) as eluent. The pure fractions were collected and the eluent was evaporated. The residue was crystallized from 2-propanone. The product was filtered off and dried, yielding 1.9 parts (49.5%) of 6-[(1H-imidazol-1-yl)(2-thienyl)methyl]-1-methyl-1H-benzotriazole; mp. 157.2° C. (compound 68). In a similar manner there were also prepared:

6-[(1H-imidazol-1-yl)(3-thienyl)methyl]-1-methyl-1H-benzotriazole; mp. 160.5° C. (compound 69);

5-[bis-(1H-imidazol-1-yl)methyl]-1-butyl-1H-benzotriazole; mp. 180.1° C. (compound 70); and 5-[1-(1H-imidazol-1-yl)-2-butynyl]-1-methyl-1H-benzotriazole; mp. 155.5° C. (compound 71).

Example 25

A mixture of 1.6 parts of 4-(1H-imidazol-1-ylmethyl)-N²-phenyl-1,2-benzenediamine, 20 parts of acetic acid and 1.08 parts of concentrated hydrochloric acid was cooled in an ice bath at 12°-16° C. A solution of 0.83 parts of sodium nitrite in 7 parts of water was added dropwise. Upon complete addition, the reaction mixture was allowed to reach room temperature while stirring. The reaction mixture was poured into alkaline ice water and the product was extracted with dichloromethane. The extract was dried, filtered and evaporated. The residue was purified by column chromatography over silica gel first using a mixture of trichloromethane and methanol, saturated with ammonia, (97.5:2.5 by volume) and then a mixture of ethyl acetate, methanol and methanol, saturated with ammonia (95:2.5:2.5 by volume) as eluents. The pure fractions were collected and the eluent was evaporated. The residue was taken up in a mixture of 2-propanone and 2,2'-oxybispropane. The product was filtered off, washed with 2,2'-oxybispropane and dried in vacuo at 60° C., yielding 0.81 parts (49.0%) of 6-(1H-imidazol-1-ylmethyl)-1-phenyl-1H-benzotriazole; mp. 110.1° C. (compound 72).

In a similar manner there were also prepared:
1-cyclohexyl-6-(1H-imidazol-1-ylmethyl)-1H-benzotriazole; mp. 109.3° C. (compound 73);
1-butyl-5-[(1H-imidazol-1-yl)phenylmethyl]-1H-benzotriazole; mp. 83.6° C. (compound 74);
1-butyl-6-[(1H-imidazol-1-yl)phenylmethyl]-1H-benzotriazole ethanedioate(1:1); mp. 109.0° C. (compound 75);
6-[(1H-imidazol-1-yl)phenylmethyl]-1-(1-methylethyl)-1H-benzotriazole ethanedioate(1:1); mp. 123.1° C. (compound 76);
6-[(4-chlorophenyl)(1H-imidazol-1-yl)methyl]-1-phenyl-1H-benzotriazole mononitrate; mp. 166.7° C. (compound 77);
6-[(4-chlorophenyl)(1H-imidazol-1-yl)methyl]-1-(phenylethyl)-1H-benzotriazole mononitrate; mp. 160.7° C. (compound 78); and
6-[(4-chlorophenyl)(1H-imidazol-1-yl)methyl]-1-[(4-chlorophenyl)methyl]-1H-benzotriazole mononitrate; mp. 185.9° C. (compound 79).

Example 26

To a stirred and cooled (0° C.) mixture of 3.9 parts of 4-(1H-imidazol-1-ylmethyl)-N²-(phenylmethyl)-1,2-benzenediamine and 9.6 parts of concentrated hydrochloric acid was added dropwise a solution of 1.86 parts of sodium nitrite in 8 parts of water. Upon complete addition, stirring was continued for 10-15 minutes at this low temperature. The reaction mixture was allowed to reach room temperature and poured into ice water. The whole was extracted with dichloromethane. The acid aqueous layer was treated with a concentrated ammonium hydroxide solution while cooling and the product was extracted with dichloromethane. The extract was dried, filtered and evaporated. The residue was purified by filtration over silica gel using a mixture of trichloromethane and methanol (95:5 by volume) as eluent. The pure fractions were collected and the eluent was evaporated. The residue was further purified by column chromatography over silica gel using a mixture of ethyl acetate, methanol and methanol, saturated with ammonia (95:2.5:2.5 by volume) as eluent. The pure fractions were collected and the eluent was evaporated. The product was filtered off, washed with 2,2'-oxybispropane and dried in vacuo at 50° C., yielding 1.6 parts (40.9%) of 6-(1H-imidazol-1-ylmethyl)-1-(phenylmethyl)-1H-benzotriazole; mp. 85.4° C. (compound 80).

In a similar manner there were also prepared:

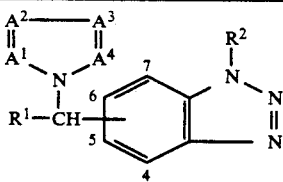

| Comp. No. | $R^1$ | $R^2$ | $A^1=A^2-A^3=A^4$ | P | base/salt | mp (°C.) |
|---|---|---|---|---|---|---|
| 81 | H— | CH₃— | CH=CH—N=CH | 5 | base | 141.6 |
| 82 | CH₃— | CH₃— | CH=CH—N=CH | 5 | base | 147.5 |
| 83 | CH₃— | CH₃—(CH₂)₃— | CH=CH—N=CH | 5 | (COOH)₂ | 108.4 |
| 84 | H— | CH₃— | CH=CH—N=CH | 6 | base | 159.5 |
| 85 | H— | cyclopropyl | CH=CH—N=CH | 6 | base | 108.4 |
| 86 | H— | cyclohexyl | CH=CH—N=CH | 5 | base | 149.4 |
| 87 | H— | (CH₃)₂—CH— | CH=CH—N=CH | 6 | base | 188.6 |
| 88 | H— | C₆H₅—CH₂— | CH=CH—N=CH | 5 | base | 130.5 |
| 89 | H— | CH₃—CH₂—CH₂— | CH=CH—N=CH | 6 | base | 113.9 |
| 90 | phenyl | CH₃— | CH=CH—N=CH | 6 | base | 105.5 |
| 91 | H— | 4-Cl—C₆H₄—CH₂— | CH=CH—N=CH | 6 | base | 117.6 |
| 92 | H— | C₆H₅—CH₂—CH₂— | CH=CH—N=CH | 6 | base | 108.5 |
| 93 | H— | (CH₃)₂—CH—(CH₂)₂— | CH=CH—N=CH | 6 | HNO₃ | 164.3-165.6 |
| 94 | H— | CH₃—CH₂—CH₂— | CH=CH—N=CH | 5 | base | 89.6 |
| 95 | H— | (CH₃)₂—CH— | CH=CH—N=CH | 5 | base | 163.0 |
| 96 | H— | C₆H₅—CH₂—CH₂— | CH=CH—N=CH | 5 | base | 96.6 |
| 97 | H— | C₆H₁₁—CH₂— | CH=CH—N=CH | 6 | base | 108.3 |
| 98 | H— | 4-F—C₆H₄—CH₂— | CH=CH—N=CH | 6 | base | 101.8 |
| 99 | H— | 3-F—C₆H₄—CH₂— | CH=CH—N=CH | 6 | base | 110.0 |
| 100 | H— | cycloheptyl | CH=CH—N=CH | 6 | base | 110.6 |
| 101 | H— | CH₃—CH₂—(CH₃)CH— | CH=CH—N=CH | 6 | HNO₃ | 165.3 |
| 102 | H— | CH₃—CH₂— | CH=CH—N=CH | 6 | base | 96.7 |
| 103 | H— | bicyclo[2.2.1]- | CH=CH—N=CH | 6 | HNO₃ | 155.5-156.7 |

-continued

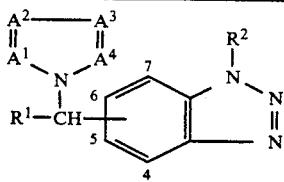

| Comp. No. | R¹ | R² | A¹=A²—A³=A⁴ | P | base/salt | mp (°C.) |
|---|---|---|---|---|---|---|
| 104 | phenyl | hept-2-yl cyclcohexyl | CH=CH—N=CH | 6 | base | 119.0 |
| 105 | H— | 1,2,3,4-tetrahydro-1-naphtalenyl | CH=CH—N=CH | 6 | (COOH)₂ | 166.1 |
| 106 | H— | CH₂=CH—CH₂— | CH=CH—N=CH | 6 | base | 114.2 |
| 107 | H— | cyclcopentyl | CH=CH—N=CH | 6 | H₂O | 108.8–111.7 |
| 108 | H— | cyclopropyl-CH₂— | CH=CH—N=CH | 6 | base | 150.2 |
| 109 | H— | HO—CH₂—CH₂—CH₂— | CH=CH—N=CH | 6 | base | 122.5 |
| 110 | phenyl | C₆H₅—CH₂— | CH=CH—N=CH | 6 | HNO₃ | 177.7 |
| 111 | H— | 2-thienyl-CH₂— | CH=CH—N=CH | 6 | base | 117.6 |
| 112 | H— | (CH₃)₃—C—CH₂— | CH=CH—N=CH | 6 | HNO₃ | 170.4 |
| 113 | 4-F—C₆H₄— | H— | CH=CH—N=CH | 5 | base | 98.6 |
| 114 | H— | (CH₃)₂—CH—(CH₂)₂— | CH=CH—N=CH | 6 | 2 HNO₃ | 162.9 |
| 115 | H— | 2,3-dihydro-1H-inden-1-yl | CH=CH—N=CH | 6 | HNO₃ | 131.1 |
| 116 | 4-Cl—C₆H₄— | (CH₃)₂—CH— | CH=CH—N=CH | 6 | base | 132.5 |
| 117 | 4-Cl—C₆H₄— | cyclcohexyl | CH=CH—N=CH | 6 | base | 162.0 |
| 118 | 3-pyridinyl | H— | CH=CH—N=CH | 6 | 2 HCl | 235.2 |
| 119 | 1H-imidazol-1-yl | H— | CH=CH—N=CH | 5 | 2 HCl | 260.4 |
| 120 | 4-Cl—C₆H₄— | (CH₃)₂—CH—(CH₂)₂— | CH=CH—N=CH | 6 | HCl 0.5 H₂O | 163.8 |
| 121 | 3-Cl—C₆H₄— | H— | CH=CH—N=CH | 5 | base | 110.6 |
| 122 | 3-F—C₆H₄— | H— | CH=CH—N=CH | 5 | base | 170.9 |
| 123 | 4-Cl—C₆H₄— | (5-methyl-2-furanyl)methyl | CH=CH—N=CH | 6 | base | residue |
| 124 | 4-Cl—C₆H₄— | H— | CH=CH—N=CH | 5 | base | 164.9 |
| 125 | i-C₃H₇— | H— | CH=CH—N=CH | 5 | base | 175.3 |
| 126 | 4-Cl—C₆H₄— | C₆H₅-methyl | CH=CH—N=CH | 5 | HCl/0.5 H₂O | 188.6 |
| 127 | 4-Cl—C₆H₄— | cyclopropyl | CH=CH—N=CH | 5 | (COOH)₂ | 117 |
| 128 | CH₃ | C₆H₅ethyl | CH=CH—N=CH | 6 | * | |
| 129 | 4-F—C₆H₄— | H— | —N=CH—N=CH | 6 | | |
| 130 | 4-Cl—C₆H₄— | H— | —N=CH—N=CH | 6 | | |
| 131 | 2-thienyl | H— | —N=CH—N=CH | 6 | | |
| 132 | 4-F—C₆H₄— | CH₃— | —N=CH—N=CH | 6 | | |
| 133 | 3-F—C₆H₄— | CH₃— | —N=CH—N=CH | 6 | | |
| 134 | 4-CH₃—C₆H₄— | CH₃— | —N=CH—N=CH | 6 | | |
| 135 | 4-CH₃O—C₆H₄— | CH₃— | —N=CH—N=CH | 6 | | |
| 136 | 4-Cl—C₆H₄— | CH₃—CH₂— | —N=CH—N=CH | 6 | | |
| 137 | 4-Cl—C₆H₄— | CH₃—CH₂—CH₂— | —N=CH—N=CH | 6 | | |
| 138 | 4-Cl—C₆H₄— | CH₃—(CH₃)CH— | —N=CH—N=CH | 6 | | |
| 139 | 4-Cl—C₆H₄— | c-C₆H₁₁— | —N=CH—N=CH | 6 | | |
| 140 | 4-Cl—C₆H₄— | C₆H₅—CH₂— | —N=CH—N=CH | 6 | | |
| 141 | 1,2,4-triazol-1-yl | CH₃— | —N=CH—N=CH | 6 | | |
| 142 | 4-F—C₆H₄— | H— | CH=N—N=CH | 6 | | |
| 143 | 4-Cl—C₆H₄— | H— | CH=N—N=CH | 6 | | |
| 144 | 4-F—C₆H₄— | CH₃— | CH=N—N=CH | 6 | | |
| 145 | 4-Cl—C₆H₄— | CH₃—(CH₃)CH— | CH=N—N=CH | 6 | | |

*(±)-2,3-dihydrobutanedioate (1:1)

Example 27

To a stirred and cooled (5° C.) solution of 5.2 parts of 4-[(1H-imidazol-1-yl)phenylmethyl]-1,2-benzenediamine in 4.8 parts of acetic acid and 20 parts of water was added a solution of 1.38 parts of sodium nitrite in 10 parts of water. The whole was stirred for 1 hour at room temperature. The reaction mixture was treated with a sodium hydrogen carbonate solution and the product was extracted with dichloromethane. The extract was dried, filtered and evaporated. The residue was crystallized from 64 parts of ethyl acetate. The product was filtered off and dried, yielding 4.7 parts (85.3%) of 5-[(1H-imidazol-1-yl)phenylmethyl]-1H-benzotriazole; mp. 178.8° C. (compound 146).

In a similar manner there were also prepared:
1-butyl-6-(1H-imidazol-1-ylmethyl)-1H-benzotriazole; mp. 49.2° C. (compound 147); and
1-butyl-5-(1H-imidazol-1-ylmethyl)-1H-benzotriazole; mp. 74.3° C. (compound 148).

Example 28

A mixture of 4.3 parts of 1-[1-(4-chloro-3-nitrophenyl)ethyl]-1H-imidazole, 3.42 parts of hydrazine monohydrate and 40 parts of 1-butanol was stirred for 12 hours at reflux temperature. After cooling, 3.4 parts of a hydrochloric acid solution 10N were added. The separated organic layer was evaporated. The residue was stirred in ethyl acetate. The product was filtered off and dried, yielding 4.5 parts (99.0%) of 6-[1-(1H- imidazol-1-yl)ethyl]-1H-benzotriazol-1-ol monohydrochloride (compound 149).

In a similar manner there was also prepared:

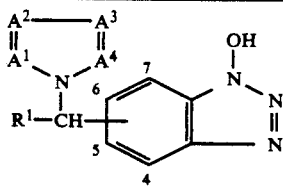

| Comp. No. | R¹ | —A¹=A²—A³=A⁴— | P | base/salt | mp (°C.) |
|---|---|---|---|---|---|
| 150 | phenyl | —CH=CH—N=CH— | 5 | base | residue |
| 151 | H— | —CH=CH—N=C(CH₃)— | 6 | base | 157 |
| 152 | H— | —N=CH—N=CH— | 6 | base | 222 |
| 153 | phenyl | —N=CH—N=CH— | 6 | base | 185 |
| 154 | phenyl | —CH=C(CH₃)—N=CH— | 6 | base | 200 |
| 155 | phenyl | —C(CH₃)=CH—N=CH— | 6 | base | residue |
| 156 | H— | —CH=CH—N=CH— | 5 | base | residue |
| 157 | phenyl | —CH=CH—N=CH— | 6 | HCl | residue |

Example 29

A mixture of 6.5 parts of 1-[(4-fluoro-3-nitrophenyl)methyl]-1H-imidazole, 6.01 parts of hydrazine monohydrate and 80 parts of ethanol was stirred and refluxed for 5 hours. After cooling, 12 parts of a hydrochloric acid solution 5N were added. The whole was evaporated. The residue was stirred with 30 parts of water and the precipitated product was filtered off and boiled in 40 parts of 2-propanol. 2-Propanol, saturated with hydrogen chloride, was added. The salt was allowed to crystallize at room temperature. It was filtered off and dried, yielding 4.1 parts (54.3%) of 6-(1H-imidazol-1-ylmethyl)-1H-benzotriazol-1-ol-monohydrochloride; mp. 207.4° C. (compound 158).

In a similar manner there were also prepared:
6-[(3-chlorophenyl)(1H-imidazol-1-yl)methyl]-1H-benzotriazol-1-ol (compound 159).

Example 30

A mixture of 3.2 parts of 6-(1H-imidazol-1-ylmethyl)-1H-benzotriazol-1-ol, 1 part of potassium carbonate and 27 parts of N,N-dimethylformamide was stirred for 30 minutes at room temperature. 2.1 Parts of 1-(chloromethyl)-3-methylbenzene were added and stirring was continued for 3 hours at room temperature. The mixture was allowed to stand overnight at room temperature and was evaporated. The residue was diluted with water and the product was extracted with dichloromethane. The extract was dried, filtered and concentrated. The concentrate was purified by column chromatography over silica gel using a mixture of trichloromethane and methanol (95:5 by volume) as eluent. The pure fractions were collected and the eluent was evaporated. The solid residue was crystallized from a mixture of ethyl acetate and 2,2'-oxybispropane (10:20 by volume). The product was filtered off, washed with 2,2'-oxybispropane and dried, yielding 3.4 parts (70.9%) of 6-(1H-imidazol-1-ylmethyl)-1-[(3-methylphenyl)methoxy]-1H-benzotriazole; mp. 120.1° C. (compound 160). In a similar manner there were also prepared:

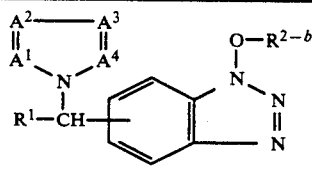

| Comp. No. | R¹ | R²⁻ᵇ | —A¹=A²—A³=A⁴— | base/salt | mp (°C.) |
|---|---|---|---|---|---|
| 161 | H— | CH₃—CH₂— | —CH=CH—N=CH— | base | 108.5 |
| 162 | H— | 2-CH₃—C₆H₄—CH₂— | —CH=CH—N=CH— | base | 134.6 |
| 163 | H— | 4-CH₃—C₆H₄—CH₂— | —CH=CH—N=CH— | base | 109.4 |
| 164 | H— | 2-F—C₆H₄—CH₂— | —CH=CH—N=CH— | base | 105.8 |
| 165 | H— | C₆H₅—O—(CH₂)₃— | —CH=CH—N=CH— | (COOH)₂ | 154.1 |
| 166* | H— | C₆H₅—CH=CH—CH₂— | —CH=CH—N=CH— | (COOH)₂ | 102.2 |
| 167 | H— | C₆H₅—O—CH₂—CH₂— | —CH=CH—N=CH— | base | 124.1 |
| 168 | H— | 3-CH₃O—C₆H₄—CH₂— | —CH=CH—N=CH— | base | 118.9 |
| 169 | H— | 4-F—C₆H₄—CH₂— | —CH=CH—N=CH— | base | 126.2 |
| 170 | H— | 3-F—C₆H₄—CH₂— | —CH=CH—N=CH— | base | 114.4 |
| 171 | H— | (C₆H₅)₂—CH— | —CH=CH—N=CH— | (COOH)₂ | 163.4 |
| 172 | H— | 2-CH₃O—C₆H₄—CH₂— | —CH=CH—N=CH— | base | 127.2 |
| 173 | H— | 4-CH₃O—C₆H₄—CH₂— | —CH=CH—N=CH— | base | 92.6 |
| 174 | H— | 2-thienyl-CH₂— | —CH=CH—N=CH— | base | 126.5 |
| 175 | H— | (CH₃)₂—N—CH₂—CH₂— | —CH=CH—N=CH— | 2HCl | 230.1 |
| 176 | H— | C₆H₅—S—CH₂— | —CH=CH—N=CH— | base | 118.0 |
| 177 | H— | 1-naphthalenyl-CH₂— | —CH=CH—N=CH— | base | 158.0 |
| 178 | H— | HO—CH₂—CH₂—CH₂— | —CH=CH—N=CH— | base | 137.0 |
| 179 | H— | CH≡C—CH₂— | —CH=CH—N=CH— | base | 130.0 |
| 180 | H— | F₃C—CH₂— | —CH=CH—N=CH— | base | 91.7 |
| 181 | H— | C₆H₄—S—CH₂—CH₂— | —CH=CH—N=CH— | base | 84.2 |
| 182 | H— | 2-pyrimidinyl | —CH=CH—N=CH— | base | 167.7 |
| 183 | H— | cyclo-C₃H₅—CH₂— | —CH=CH—N=CH— | HNO₃ | 136.5 |
| 184 | H— | cyclo-C₆H₁₁—CH₂— | —CH=CH—N=CH— | HNO₃ | 149.0 |

-continued

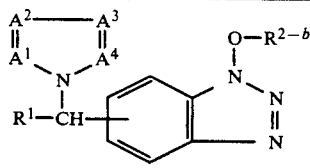

| Comp. No. | R¹ | R²⁻ᵇ | —A¹=A²—A³=A⁴— | base/salt | mp (°C.) |
|---|---|---|---|---|---|
| 185 | H— | CH₃—CH₂— | —CH=CH—N=C—<br>                 \|<br>                CH₃ | base | 93.6 |
| 186 | H— | CH₃—CH₂— | —N=CH—N=CH— | base | 116.9 |
| 187 | H— | CH₃—CH₂—CH₂—CH₂— | —CH=CH—N=C—<br>                 \|<br>                CH₃ | HNO₃ | 95.1 |
| 188 | phenyl | C₆H₅—CH₂— | —CH=CH—N=CH— | (COOH)₂ | 152.5 |
| 189 | phenyl | C₆H₅—CH₂— | —CH=CH—N=CH— | base | 113.2 |
| 190 | H— | (2-oxo-2,3-dihydro-1H-benzimidazol-1-yl)propyl | —CH=CH—N=CH— | base | 210.3 |
| 191 | H— | C₆H₅—C₆H₄—CH₂— | —CH=CH—N=CH— | base | 133.0 |
| 192 | H— | (1H-benzimidazol-2-yl)methyl | —CH=CH—N=CH— | base | 212.5 |
| 193 | H— | (2-methyl-1H-benzimidazol-5-yl)methyl | —CH=CH—N=CH— | base | 209.1 |
| 194 | H— | (2,3-dihydro-1,4-benzodioxin-2-yl)methyl | —CH=CH—N=CH— | (COOH)₂ | 171.6 |

* = E-form

Example 31

A mixture of 3.23 parts of 6-(1H-imidazol-1-ylmethyl)-1H-benzotriazol-1-ol, 2.07 parts of potassium carbonate and 20 parts of dimethyl sulfoxide was stirred for 10 minutes at room temperature. Then there were added 2.55 parts of 2-iodopropane and stirring was continued first for 15 minutes at room temperature and then for 1 hour at 50° C. The reaction mixture was evaporated. 50 Parts of water were added. The product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from 14 parts of 1,1'-oxybisethane. The product was filtered off and dried, yielding 3.3 parts (85.5%) of 6-(1H-imidazol-1-ylmethyl)-1-(1-methylethoxy)-1H-benzotriazole; mp. 114.3° C. (compound 195).

In a similar manner there were also prepared:

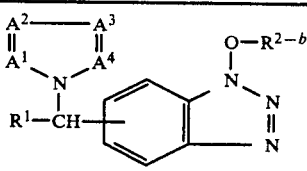

| Comp. No. | R¹ | R²⁻ᵇ | —A¹=A²—A³=A⁴— | base/salt | mp (°C.) |
|---|---|---|---|---|---|
| 196 | H— | 3-pyridinyl-CH₂— | —CH=CH—N=CH— | base | 120.6 |
| 197 | H— | CH₃—CH₂—(CH₃)CH— | —CH=CH—N=CH— | HNO₃ | 133.3 |
| 198 | H— | CH₃—CH₂—O—C(=O)—CH₂— | —CH=CH—N=CH— | HNO₃ | 143.3 |
| 199 | H— | CH₃—CH₂—O—C(=O)—(CH₂)₄— | —CH=CH—N=CH— | base | oil |
| 200 | H— | CH₃—CH₂—O—C(=O)—(CH₂)₃— | —CH=CH—N=CH— | base | oil |
| 201 | H— | CH₃—(CH₂)₄— | —CH=CH—N=CH— | HNO₃ | 115.2 |
| 202 | H— | CH₃—(CH₂)₅— | —CH=CH—N=CH— | HNO₃ | 93.9 |
| 203 | H— | CH₃—(CH₂)₈— | —CH=CH—N=CH— | HNO₃ | 90.0 |
| 204 | H— | Br—(CH₂)₂— | —CH=CH—N=CH— | HNO₃ | 131.3 |
| 205 | H— | 2-pyridinyl-CH₂— | —CH=CH—N=CH— | base | 81.7 |
| 206 | H— | CH₃—(CH₂)₆— | —CH=CH—N=CH— | HNO₃ | 80.7 |

-continued

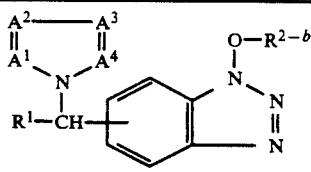

| Comp. No. | R¹ | R²⁻ᵇ | —A¹=A²—A³=A⁴— | base/salt | mp (°C.) |
|---|---|---|---|---|---|
| 207 | H— | C₆H₅—(CH₂)₃— | —CH=CH—N=CH— | (COOH)₂ | 135.7 |
| 208 | H— | C₆H₅—(CH₂)₂— | —CH=CH—N=CH— | (COOH)₂ | 136.0 |
| 209 | H— | 1-methyl-4-piperidinyl | —CH=CH—N=CH— | 2HNO₃ | 176.9 |
| 210 | CH₃— | CH₃—CH₂—O—C(=O)—CH₂— | —CH=CH—N=CH— | base | residue |
| 211 | phenyl | CH₃—CH₂— | —N=CH—N=CH— | 0.5(COOH)₂ | 92.1 |
| 212 | phenyl | CH₃—CH₂— | —CH=C(CH₃)—N=CH— | HNO₃ | 125.8 |
| 213 | phenyl | C₆H₅—CH₂— | —C(CH₃)=CH—N=CH— | base | 156.2 |
| 214 | phenyl | CH₃—CH₂—CH₂—CH₂— | —CH=C(CH₃)—N=CH— | HNO₃ | 126.9 |

Example 32

A mixture of 4.5 parts of 6-[1-(1H-imidazol-1-yl)ethyl]-1H-benzotriazol-1-ol monohydrochloride, 3.12 parts of iodoethane, 3.7 parts of sodium carbonate and 63 parts of N,N-dimethylformamide was stirred for 4 hours at room temperature. The reaction mixture was evaporated and the residue was taken up in water. The product was extracted with methylbenzene. The extract was dried, filtered and evaporated. The residue was crystallized from a mixture of 27 parts of ethyl acetate and 21 parts of 2,2'-oxybispropane. The product was filtered off and dried, yielding 2.26 parts (51.6%) of 1-ethoxy-6-[1-(1H-imidazol-1-yl)ethyl]-1H-benzotriazole; mp. 81.1° C. (compound 215).

In a similar manner there were also prepared:
5-[(1H-imidazol-1-yl)phenylmethyl]-1-(1-methylethoxy)-1H-benzotriazole; mp. 85.7° C. (compound 216);
1-ethoxy-5-[(1H-imidazol-1-yl)phenylmethyl]-1H-benzotriazole; mp. 85.5° C. (compound 217);
6-[1-(1H-imidazol-1-yl)ethyl]-1-(phenylmethoxy)-1H-benzotriazole; mp. 128.6° C. (compound 218); and
6-[1-[(1H-imidazol-1-yl)ethyl]-1-(2-methoxyethoxy)-1H-benzotriazole (±)-2,3-dihydroxybutanedioate; mp. 140.0° C. (compound 219).

Example 33

To a stirred and heated (50° C.) mixture of 2.81 parts of 6-(1H-imidazol-1-ylmethyl)-1H-benzotriazol-1-ol and 22.5 parts of N,N-dimethylformamide were added 0.69 parts of a sodium hydride dispersion. The reaction mixture was stirred until hydrogen evolution had ceased. 1.28 Parts of 1-chloro-2-methoxyethane were added at room temperature and stirring was continued for a while. 22 Parts of dimethyl sulfoxide and 0.04 parts of 2-(2-methoxyethoxy)-N,N-bis[2-(2-methoxyethoxy)ethyl]ethanamine were added. The reaction mixture was stirred overnight at 50° C. and then poured into water. The product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from a mixture of ethyl acetate and 2,2'-oxybispropane (1:3 by volume). The product was filtered off, washed with a mixture of ethyl acetate and 2,2'-oxybispropane (1:3 by volume) and 2,2'-oxybispropane and dried in vacuo at 50° C., yielding 1.66 parts (46.7%) of 6-(1H-imidazol-1-ylmethyl)-1-(2-methoxyethoxy)-1H-benzotriazole; mp. 77.0° C. (compound 220).

Example ÷

To a stirred mixture of 4.5 parts of 5-(1H-imidazol-1-ylmethyl)-1H-benzotriazol-1-ol and 94 parts of N,N-dimethylformamide was added portionwise 1 part of a sodium hydride dispersion 50%. Upon complete addition, stirring was continued till hydrogen evolution had ceased. 1.3 Parts of iodomethane were added at once and stirring was continued at room temperature. The N,N-dimethylformamide formamide layer was evaporated and the residue was taken up in water and a mixture of trichloromethane, methanol and methanol, saturated with ammonia (90:5:5 by volume). The product was extracted with a mixture of trichloromethane, methanol and methanol, saturated with ammonia (90:5:5 by volume). The extract was dried, filtered and evaporated. The residue was purified by column chromatography over silica gel first using trichloromethane and then a mixture of trichloromethane and methanol (90:10 by volume) as eluents. The pure fractions were collected and the eluent was evaporated. The residue was stirred in 2,2'-oxybispropane. The product was filtered off and dried in vacuo at 50° C., yielding 3.1 parts (64.3%) of 5-(1H-imidazol-1-ylmethyl)-1-methoxy-1H-benzotriazole; mp. 94.3° C. (compound 221).

In a similar manner there was also prepared:
5-(1H-imidazol-1-ylmethyl)-1-(phenylmethoxy)-1H-benzotriazole; mp. 113.7° C. (compound 222);
6-[(3-chlorophenyl) (1H-imidazol-1-yl)methyl]-1-(phenylmethoxy)-1H-benzotriazole ethanedioate(2:3); mp. 169.3° C. (compound 223); and 1-butoxy-6-[(3-chlorophenyl) (1H-imidazol-1-yl)methyl]-1H-benzotriazole ethanedioate (1:1); mp. 96.5° C. (compound 224).

Example 35

To a stirred solution of 0.46 parts of sodium in 24 parts of methanol were added 4.3 parts of 6-(1H-imidazol-1-ylmethyl)-1H-benzotriazol-1-ol. The mixture was stirred for 10 minutes and then evaporated. 9 Parts of methylbenzene were added to the residue and the whole was evaporated again. To the residue in 9 parts of N,N-dimethylformamide was added a solution of 3.12 parts of iodoethane in 4.5 parts of N,N-dimethylformamide. The whole was stirred for 1 hour at 50° C. and evaporated. 60 Parts of water were added and the product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in 2-propanol and 4-methyl-2-pentanone. The salt was filtered off and dried, yielding 4.5 parts (80%) of 1-ethoxy-6-(1H-imidazol-1-ylmethyl)-1H-benzotriazole monohydrochloride; mp. 140.2° C. (compound 225).

In a similar manner there were also prepared:
1-butoxy-6-(1H-imidazol-1-ylmethyl)-1H-benzotriazole monohydrochloride; mp. 124.2° C. (compound 226);
6-(1H-imidazol-1-ylmethyl)-1-propoxy-1H-benzotriazole monohydrochloride. hemihydrate; mp. 130.5° C. (compound 227); and
6-(1H-imidazol-1-ylmethyl)-1-(phenylmethoxy)-1H-benzotriazole; mp. 113.8° C. (compound 228).

Example 36

To a stirred suspension of 4.7 parts of 6-(1H-imidazol-1-ylmethyl)-1H-benzotriazol-1-ol in 60 parts of ethanol were added 22.5 parts of a sodium hydroxide solution 1N. The whole was stirred till a clear solution was obtained. The mixture was evaporated to dry. The residue was dissolved in 18 parts of N,N-dimethylformamide. To the thus obtained solution was added at once a solution of 3.2 parts of iodomethane in 9 parts of N,N-dimethylformamide. After stirring for 30 minutes at room temperature, the whole was evaporated. The residue was purified by column chromatography over silica gel using a mixture of trichloromethane and methanol (95:5 by volume) as eluent. The pure fractions were collected and the eluent was evaporated. The residue was crystallized from 8 parts of 4-methyl-2-pentanone. The product was filtered off and dried, yielding 3.3 parts (65.4%) of 6-(1H-imidazol-1-ylmethyl)-1-methoxy-1H-benzotriazole; mp. 132.4° C. (compound 229).

Example 37

A mixture of 5.85 parts of 6-[phenyl(1H-1,2,4-triazol-1-yl)methyl]-1H-benzotriazol-1-ol, 1.4 parts of potassium carbonate and 27.5 parts of dimethyl sulfoxide was stirred for 30 minutes at 50° C. After cooling, 3.55 parts of ethyl 2-bromoacetate were added and the whole was stirred for 2 hours at room temperature. Another portion of 1.4 parts of potassium carbonate was added. After stirring for 3 hours at 50° C., the mixture was cooled and 2.0 parts of concentrated hydrochloric acid were added. The dimethyl sulfoxide layer was evaporated. The residue was taken up in 25 parts of water and 130 parts of dichloromethane. The separated organic layer was dried, filtered and evaporated. The residue was purified by column chromatography over silica gel using a mixture of trichloromethane, methanol and methanol, saturated with ammonia, (92:4:4 by volume) as eluent. The pure fractions were collected and the eluent was evaporated. The residue was crystallized from 20 parts of 4-methyl-2-pentanone. The product was filtered off and dried, yielding 4.4 parts (79.6%) of 5-[phenyl(1H-1,2,4-triazol-1-yl)methyl]-1H-benzotriazole; mp. 182.7° C. (compound 230).

In a similar manner there were also prepared:
5-[1-(1H-imidazol-1-yl)ethyl]-1H-benzotriazole; mp. 165.3° C. (compound 231);
5-[(2-methyl-1H-imidazol-1-yl)methyl]-1H-benzotriazole; mp. 214.3° C. (compound 232); and
5-[(4-methyl-1H-imidazol-1-yl)phenylmethyl]-1H-benzotriazole; mp. 166.7° C. (compound 233).

Example 38

A mixture of 4.3 parts of 6-(1H-imidazol-1-ylmethyl)-1H-benzotriazol-1-ol monohydrochloride and 120 parts of methanol was hydrogenated at normal pressure and at 50° C. with 2 parts of platinium-on-charcoal catalyst 5%. After the calculated amount of hydrogen was taken up, the catalyst was filtered off and the filtrate was evaporated. The residue was crystallized twice from ethanol. The product was filtered off and dried, yielding 2.9 parts (72%) of 5-(1H-imidazol-1-ylmethyl)-1H-benzotriazole monohydrochloride; mp. 230.4° C. (compound 234).

Example 39

2.47 Parts of 5-(1H-imidazol-1-ylmethyl)-1H-benzotriazole were added portionwise to 30 parts of fuming nitric acid while stirring. Upon complete addition, stirring was continued overnight at room temperature. The reaction mixture was poured into 100 parts of crushed ice and nitrogen was bubbled through the mixture during 30 minutes. The precipitated product was filtered off, washed with water and purified by reversed phase chromatography (HPLC) over Li Chroprep RP 18 using a mixture of methanol, acetonitrile and an ammonium acetate solution 0.5% (17:8:75 by volume) as eluent. The desired fraction was collected and the eluent was evaporated. The residue was stirred in methanol and 2,2'-oxybispropane. The precipitated product was filtered off and boiled in methanol. The product was filtered off, washed with methanol and 2,2'-oxybispropane and dried in vacuo at 50°-60° C., yielding 0.05 parts (1.6%) of 5-(1H-imidazol-1-ylmethyl)-6-nitro-1H-benzotriazole; mp. 286.0° C. (decomp.) (compound 235).

Example 40

A mixture of 3.2 parts of ethyl 4-[[6-(1H-imidazol-1-ylmethyl)-1H-benzotriazol-1-yl]oxy]butanoate, 25 parts of a sodium hydroxide solution 1N and 20 parts of ethanol was stirred for 1.5 hours at room temperature. 25 Parts of a hydrochloric acid solution 1N were added and the whole was concentrated to a volume of about 20 parts. The precipitated product, which was formed during concentration, was filtered off, washed with water, 2-propanol and 1,1'-oxybisethane and dried, yielding 2.1 parts (71%) of 4-[[6-(1H-imidazol-1-ylmethyl)-1H-benzotriazol-1-yl]oxy]butanoic acid; mp. 170.5° C. (compound 236).

In a similar manner there was also prepared:

5-[[6-(1H-imidazol-1-ylmethyl)-1H-benzotriazol-1-yl]oxy]pentanoic acid; mp. 132.7° C. (compound 237).

Example 41

A solution of 7.1 parts of 6-[[4-(4,5-dihydro-4,4-dimethyl-2-oxazolyl)phenyl](1H-imidazol-1-yl)methyl]-1-methyl-1H-benzotriazole in 100 parts of a hydrochloric acid solution 3N was stirred overnight at reflux temperature. The reaction mixture was evaporated to dry, yielding 8.9 parts (100%) of 4-[(1H-imidazol-1-yl)(1-methyl-1H-benzotriazol-6-yl)methyl]benzoic acid monohydrochloride as a residue (compound 238).

Example 42

A solution of 8.9 parts of 4-[(1H-imidazol-1-yl)(1-methyl-1H-benzotriazol-6-yl)methyl]benzoic acid monohydrochloride in 32.4 parts of thionyl chloride was stirred for 1 hour at room temperature. The reaction mixture was evaporated. A solution of the residue in 80 parts of ethanol was stirred for 1 hour at 60° C. The reaction mixture was concentrated. The concentrate was taken up in a diluted potassium carbonate solution and the product was extracted with dichloromethane. The extract was dried, filtered and evaporated. The residue was purified by column chromatography over silica gel using a mixture of dichloromethane and methanol (98:2 by volume) as eluent. The pure fractions were collected and the eluent was evaporated. The residue was converted into the ethanedioate salt. The salt was filtered off and dried, yielding 1 part (8.5%) of ethyl 4-[(1H-imidazol-1-yl)(1-methyl-1H-benzotriazol-6-yl)methyl]benzoate ethanedioate(1:1); mp. 155.5° C. (compound 239).

Example 43

A mixture of 7 parts of 5-[1(1H-imidazol-1-yl)-2-butynyl]-1-methyl-1H-benzotriazole, 0.1 parts of quinoline, 54 parts of ethyl acetate and 32 parts of ethanol was hydrogenated at 931.00 Pa and at room temperature with 0.3 parts of palladium-on-charcoal catalyst 10%. After the calculated amount of hydrogen was taken up, the catalyst was filtered off over diatomaceous earth and the filtrate was evaporated. The residue was purified by column chromatography over silica gel using a mixture of dichloromethane and methanol (95:5 by volume) as eluent. The pure fractions were collected and the eluent was evaporated. The residue was crystallized from a mixture of dichloromethane and 1,1'-oxybisethane. The product was filtered off and dried, yielding 1.4 parts (19.7%) of 5-[1-(1H-imidazol-1-yl)-2-butenyl]-1-methyl-1H-benzotriazole; mp. 104° C. (compound 240).

Example 44

A mixture of 2.6 parts of 4-[(1H-imidazol-1-yl)(1-methyl-1H-benzotriazol-5-yl)methyl]benzaldehyde, 0.85 parts of hydroxylamine monohydrochloride, 16 parts of ethanol and 3.4 parts of potassium carbonate was stirred for 1 hour at 50° C. The reaction mixture was filtered and the filtrate was evaporated. The residue was purified by column chromatography over silica gel using a mixture of trichloromethane and methanol (95:5 by volume) as eluent. The pure fractions were collected and the eluent was evaporated. The residue was crystallized from 2-propanone. The product was filtered off and dried, yielding 1.7 parts (63.9%) of 4-[(1H-imidazol-1-yl)(1-methyl-1H-benzotriazol-5-yl)methyl]benzaldehyde, oxime; mp. 149.5° C. (compound 241).

C. Pharmacological Examples

The useful inhibition of the aromatase activity of the compounds of formula (I) can be demonstrated in the following test procedures.

Example 45: In Vitro-Inhibition of the Aromatase Activity Test

For example, one may study the effect of the compounds of the present invention on the conversion of 1,2[3H]androstenedione into estrone and estradiol in the presence of human placental microsomes following procedures analogous to those described in J. Steroid Biochem., 7, 787 (1976).

Human placental microsomes were diluted in potassium phosphate buffer (0.1M, pH 7.4) to give about 50% conversion of androgens to estrogens (protein content: about 0.5 mg). Four ml human placental microsomes were incubated in a final volume of 5 ml with 0.2 $\mu$Cil, 2[3H]-androstenedione, 2 $\mu$g androstendione and 5 $\mu$l of test compound and/or dimethyl sulfoxide (DMSO). Further the incubation mixture contained a NADPH-regenerating system consisting of ATP (2,48 mM), NADP (0.97 mM), glucose-6-phosphate (8.22 mM), glucose-6-phosphate dehydrogenase (0.98 units) and $MgCl_2$ (2.46 mM). The reaction was initiated by the addition of androstenedione and proceeded for 30 min at 37° C. During the incubation period, the mixtures were gassed with air. In this assay, aromatization of androstenedione results in the production of [3H]-$H_2O$ which is isolated by extracting the samples with chloroform to remove the free steroid. Samples are counted in a liquid scintillation spectrometer and the percent inhibition is determined by comparing the results with control samples incubated without inhibitor.

The effects of the compounds of the present invention are presented in table I, column (a) as the concentration in $\mu$M of the compound required to obtain 50% inhibition of the estrogen synthesis ($IC_{50}$-values).

Example 46: In Vivo-Inhibition of the Aromatase Activity

Immature female Wistar rats weighing 120 g were injected subcutaneously with 200 I.U. of pregnant mare's serum gonadotropin (PMSG). Ninety hours later, 1 mg/kg of the test compound dissolved in 0.5 ml 20% polyethyleneglycol in water was administered by oral gavage. Control animals received 20% polyethyleneglycol only. Two hours following drug or placebo administration the rats were killed by decapitation and trunk blood was collected on heparine. Plasma estradiol concentrations were measured by standard radio-immunological procedures. The percentage recovery estradiol relative to the controls are depicted in column (b) of table (I). The results in this table are not given for the purpose of limiting the invention thereto but only to exemplify the useful pharmacological properties of all the compounds within the scope of formula (I).

| Compound | $IC_{50}$-values ($\mu$M) | % recovery estradiol |
| --- | --- | --- |
| 225 | 0.0100 | 19 |
| 226 | 0.0067 | 19 |
| 227 | 0.0074 | 19 |
| 228 | 0.0052 | — |

-continued

| Compound | IC$_{50}$-values ($\mu$M) | % recovery estradiol |
|---|---|---|
| 195 | 0.0120 | 19 |
| 196 | 0.0110 | — |
| 197 | 0.0110 | — |
| 198 | 0.0180 | — |
| 201 | 0.0067 | 19 |
| 202 | 0.0071 | 21 |
| 203 | 0.0170 | — |
| 204 | 0.0092 | 19 |
| 206 | 0.0080 | — |
| 2 | 0.0160 | 20 |
| 4 | 0.0160 | — |
| 6 | 0.0120 | — |
| 207 | 0.0073 | 26 |
| 208 | 0.0110 | — |
| 7 | 0.0257 | 7 |
| 147 | 0.0076 | 21 |
| 176 | 0.0120 | — |
| 191 | 0.0234 | — |
| 179 | 0.0232 | — |
| 75 | 0.0242 | 27 |
| 76 | 0.0347 | 9 |
| 87 | 0.0269 | 5 |
| 89 | 0.0150 | 5 |
| 90 | 0.0227 | 5 |
| 91 | 0.0088 | — |
| 92 | 0.0087 | 15 |
| 15 | 0.0226 | 2 |
| 93 | 0.0105 | 8 |
| 17 | 0.0182 | 7 |
| 97 | 0.0131 | 10 |
| 99 | 0.0178 | 11 |
| 23 | 0.0075 | — |
| 100 | 0.0143 | 3 |
| 101 | 0.0174 | 7 |
| 102 | 0.0317 | 2 |
| 103 | 0.0163 | 5 |
| 28 | 0.0253 | 6 |
| 29 | 0.0159 | 7 |
| 30 | 0.0222 | 7 |
| 31 | 0.0342 | 8 |
| 104 | 0.0206 | 9 |
| 33 | 0.0246 | 5 |
| 105 | 0.0198 | 14 |
| 213 | 0.0362 | — |
| 106 | 0.0244 | 8 |
| 107 | 0.0141 | 6 |
| 108 | 0.0152 | 3 |
| 109 | 0.0262 | — |
| 188 | 0.0182 | — |
| 111 | 0.0143 | 19 |
| 113 | 0.0188 | 4 |
| 48 | 0.0166 | 6 |
| 50 | 0.0183 | 1 |
| 51 | 0.0222 | 7 |
| 115 | 0.0144 | 22 |
| 55 | 0.0188 | 3 |
| 56 | 0.0215 | 8 |
| 116 | 0.0249 | 20 |
| 64 | 0.0257 | 3 |
| 117 | 0.0125 | 9 |
| 69 | 0.0290 | 5 |
| 77 | 0.0176 | 21 |
| 220 | 0.0200 | — |
| 120 | 0.0089 | — |
| 59 | 0.0180 | — |

D) Composition Examples

The following formulations exemplify typical pharmaceutical compositions in dosage unit form suitable for systemic administration to animal and human subjects in accordance with the instant invention. "Active ingredient" (A.I.) as used throughout these examples relates to a compound of formula (I) or a pharmaceutically acceptable acid addition salt thereof.

Example 47: Oral Drops

500 Grams of the A.I. was dissolved in 0.5 liters of 2-hydroxypropanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 48: Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 49: Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 50: Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

Example 51: Injectable Solution 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

Example 52: Suppositories

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°~38° C. to form 100 suppositories each containing 30 milligrams of the active ingredient.

We claim:

1. A compound of the formula:

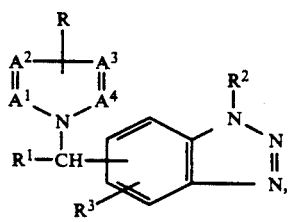
(I)

a pharmaceutically acceptable acid addition salt or a stereochemically isomeric form thereof, wherein:
—$A^1$=$A^2$—$A^3$=$A^4$— represents a bivalent group of the formula:

—CH=N—CH=CH—  (a-1),

—CH=N—CH=N—  (a-2), or

—CH=N—N=CH—  (a-3);

R represents hydrogen or $C_{1-6}$alkyl;
$R^1$ represents hydrogen, $C_{1-6}$alkyl optionally substituted with phenyl or substituted phenyl, phenyl, substituted phenyl, $C_{3-7}$cycloalkyl, pyridinyl, naphthalenyl, thienyl, furanyl, imidazolyl, triazolyl, $C_{2-6}$alkenyl, or $C_{2-6}$alkynyl;
$R^2$ represents pyrimidinyloxy; and
$R^3$ represents hydrogen or nitro,
wherein substituted phenyl is phenyl substituted with up to three substituents each independently selected from the group consisting of halo, hydroxy, hydroxymethyl, trifluoromethyl, $C_{1-6}$alkyl, $C_{1-6}$alkoxy, $C_{1-6}$alkyloxycarbonyl, carboxyl, formyl, (hydroxyimino)methyl, nitrile, amino, mono— and di($C_{1-6}$alkyl) amino, and nitro.

2. The compound of claim 1 wherein the

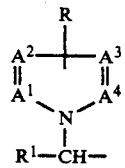

moiety is substituted on either the 5 or 6 position of the benzotriazole ring.

3. The pharmaceutical composition of claim 1 wherein the

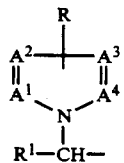

moiety is substituted on either the 5 or 6 position of the benzotriazole ring.

4. The compound of claim 1 wherein said compound is 6-(1H-imidazol-1-ylmethyl)-1-(2-pyrimidinyloxy)-1H-benzotriazole.

5. A pharmaceutical composition comprising an inert carrier and as active ingredient an estrogene hormone biosynthesis inhibitory amount of a compound of the formula:

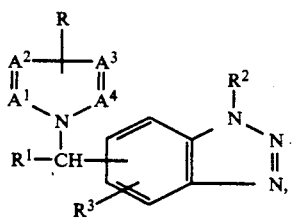
(I)

a pharmaceutically acceptable acid addition salt or a stereochemically isomeric form thereof, wherein:
—$A^1$=$A^2$—$A^3$=$A^4$— represents a bivalent group of the formula:

—CH=N—CH=CH—  (a-1),

—CH=N—CH=N—  (a-2), or

—CH=N—N=CH—  (a-3);

R represents hydrogen or $C_{1-6}$alkyl;
$R^1$ represents hydrogen, $C_{1-6}$alkyl optionally substituted with phenyl or substituted phenyl, phenyl, substituted phenyl, $C_{3-7}$cycloalkyl, pyridinyl, naphthalenyl, thienyl, furanyl, imidazolyl, triazolyl, $C_{2-6}$alkenyl, or $C_{2-6}$alkynyl;
$R^2$ represents pyrimidinyloxy; and
$R^3$ represents hydrogen or nitro,
wherein substituted phenyl is phenyl substituted with up to three substituents each independently selected from the group consisting of halo, hydroxy, hydroxymethyl, trifluoromethyl, $C_{1-6}$alkyl, $C_{1-6}$alkoxy, $C_{1-6}$alkyloxycarbonyl, carboxyl, formyl, (hydroxyimino)methyl, nitrile, amino, mono- and di($C_{1-6}$alkyl)amino, and nitro.

6. The pharmaceutical composition of claim 5 wherein said compound is 6-(1H-imidazol-1-ylmethyl)-1-(2-pyrimidinyloxy)-1H-benzotriazole.

* * * * *